(12) United States Patent
Zakrzewski et al.

(10) Patent No.: US 10,041,879 B2
(45) Date of Patent: Aug. 7, 2018

(54) IMAGING SYSTEM FOR FUEL TANK ANALYSIS

(71) Applicant: Simmonds Precision Products, Inc., Vergennes, VT (US)

(72) Inventors: Radoslaw Zakrzewski, South Burlington, VT (US); Mark Sherwood Miller, Lakeville, MN (US); Michael A. Lynch, Shelburne, VT (US)

(73) Assignee: Simmonds Prevision Products, Inc., Vergennes, VT (US)

( * ) Notice: Subject to any disclaimer, the term of this patent is extended or adjusted under 35 U.S.C. 154(b) by 224 days.

(21) Appl. No.: 15/015,859

(22) Filed: Feb. 4, 2016

(65) Prior Publication Data

US 2017/0227457 A1    Aug. 10, 2017

(51) Int. Cl.
| | |
|---|---|
| *G01N 21/00* | (2006.01) |
| *G01N 21/41* | (2006.01) |
| *G01F 23/292* | (2006.01) |
| *G01J 5/00* | (2006.01) |
| *G01N 9/24* | (2006.01) |

(Continued)

(52) U.S. Cl.
CPC ............ *G01N 21/41* (2013.01); *G01F 22/00* (2013.01); *G01F 23/0076* (2013.01); *G01F 23/292* (2013.01); *G01F 23/2928* (2013.01); *G01J 5/0037* (2013.01); *G01N 9/24* (2013.01); *G01N 21/4133* (2013.01); *G01S 7/4808* (2013.01); *H04N 5/33* (2013.01); *H04N 13/0253* (2013.01); *H04N 13/0282* (2013.01);

(Continued)

(58) Field of Classification Search
CPC .... G01F 22/00; G01F 23/0076; G01F 23/292; G01F 23/2928; G01J 5/0037; G01N 21/41; G01N 21/4133; G01N 2201/06113; G01N 2201/12; G01N 33/22; G01N 9/24; G01S 17/89; G01S 7/4808; H04N 5/33
USPC .......................................................... 356/72
See application file for complete search history.

(56) References Cited

U.S. PATENT DOCUMENTS

| 4,420,976 A | 12/1983 | Orloff et al. |
| 5,157,453 A | 10/1992 | Suzuki et al. |

(Continued)

FOREIGN PATENT DOCUMENTS

| CN | 102467846 A | | 5/2012 | |
| JP | 2008107098 | * | 5/2008 | ......... G01N 21/4133 |

(Continued)

OTHER PUBLICATIONS

Nemoto, Shojiro, "Measurement of the Refractive Index of Liquid Using Laser Beam Displacement", Applied Optics, Optical Society of America, Washington, DC; US, vol. 31, No. 31, Nov. 1, 1992, pp. 6690-6694, XP000310811, ISSN: 0003-6935.

(Continued)

*Primary Examiner* — Sunghee Y Gray
(74) *Attorney, Agent, or Firm* — Kinney & Lange, P.A.

(57) ABSTRACT

A method can include emitting, from a light source, directional light through fuel contained in a fuel tank, and determining a refraction angle of the directional light after the directional light passes through an interface with the fuel. The method can further include determining, by a processing device, an index of refraction of the fuel based on the determined refraction angle, and determining, by the processing device, a density of the fuel based on the determined index of refraction of the fuel.

14 Claims, 12 Drawing Sheets

(51) Int. Cl.
  *H04N 5/33*    (2006.01)
  *H04N 13/02*   (2006.01)
  *G01S 7/48*    (2006.01)
  *G01F 22/00*   (2006.01)
  *G01F 23/00*   (2006.01)
  *G01N 33/22*   (2006.01)
  *G01S 17/89*   (2006.01)

(52) U.S. Cl.
  CPC .... *G01N 33/22* (2013.01); *G01N 2201/06113* (2013.01); *G01N 2201/12* (2013.01); *G01S 17/89* (2013.01)

(56) References Cited

U.S. PATENT DOCUMENTS

| | | |
|---|---|---|
| 6,782,122 B1 | 8/2004 | Kline et al. |
| 8,184,848 B2 | 5/2012 | Wu et al. |
| 9,068,875 B1 | 6/2015 | Wirthlin |
| 2010/0086172 A1 | 4/2010 | Venkoparao et al. |
| 2010/0224263 A1 | 9/2010 | Riedel et al. |
| 2010/0241362 A1* | 9/2010 | Yoshikawa ........ G01N 21/553 702/24 |
| 2015/0002658 A1 | 1/2015 | Jaw et al. |
| 2015/0130929 A1 | 5/2015 | Turner et al. |
| 2015/0130930 A1 | 5/2015 | Turner et al. |
| 2015/0153212 A1 | 6/2015 | Cipullo et al. |
| 2016/0313242 A1* | 10/2016 | Margalit ........... G01N 21/4133 |

FOREIGN PATENT DOCUMENTS

| | | |
|---|---|---|
| JP | 2008107098 A | 5/2008 |
| WO | 2007049005 A1 | 5/2007 |

OTHER PUBLICATIONS

Extended European Search Report for European Patent Application No. 17153980.2, dated Jul. 12, 2017, 10 pages.

* cited by examiner

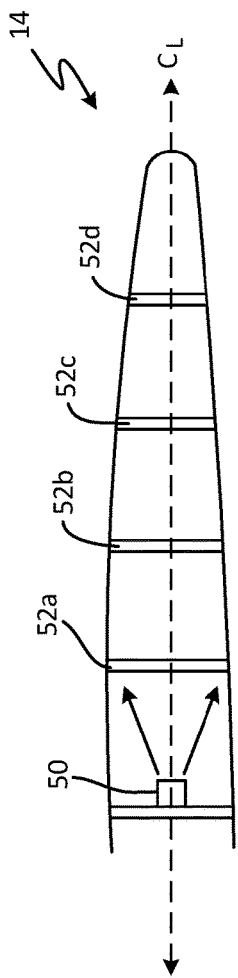
Fig. 4A
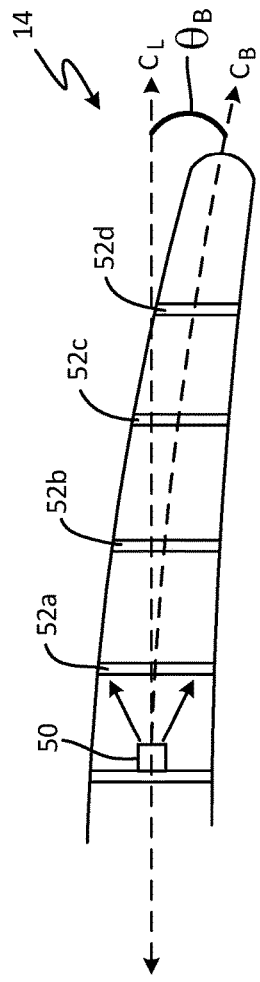
Fig. 4B
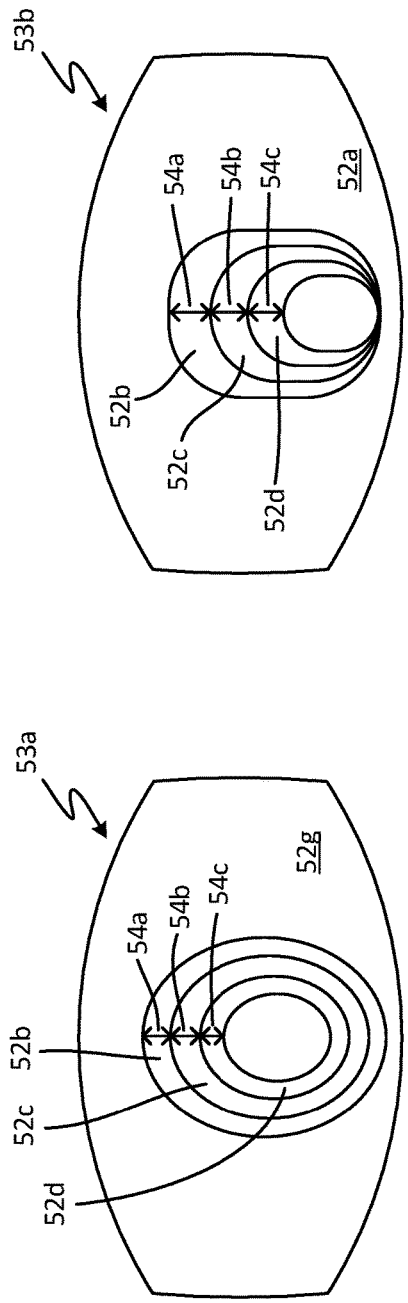
Fig. 5A
Fig. 5B

IMAGING SYSTEM FOR FUEL TANK ANALYSIS

BACKGROUND

The present invention relates to fluid storage systems, and in particular to determining properties of fuel tanks and their contents.

In fuel systems such as those on aircraft, for example, it is desirable to accurately determine properties related to fuel tanks, such as the volume and/or mass of fuel remaining. These tanks may exist in complex environments, such as the wing of the aircraft, for example. Various factors may affect the orientation of fuel within these tanks, such as tilt of the aircraft and bending of the wing. It is desirable to know how each of these factors are presently affecting a tank, so as to facilitate accurate determination of remaining fuel.

Prior art systems have implemented capacitive probes within fuel tanks, for example, to determine the volume of remaining fuel. Electromagnetic fields are utilized by the probes to determine the level of fuel within the tank, which may then be used to calculate a remaining fuel volume. However, due to strict regulations, the amount of energy permitted within a fuel tank is limited, constraining the number of probes that may be utilized. Moreover, a number of capacitive and/or other probes (e.g., densitometers, temperature probes, or other probes) required to be installed for accurate determination of a remaining fuel volume can result in significant installation and maintenance costs. Therefore, it desirable to implement an improved system for determining properties of fuel tanks.

SUMMARY

In one example, a method includes emitting, from a light source, directional light through fuel contained in a fuel tank, and determining a refraction angle of the directional light after the directional light passes through an interface with the fuel. The method can further include determining, by a processing device, an index of refraction of the fuel based on the determined refraction angle, and determining, by the processing device, a density of the fuel based on the determined index of refraction of the fuel.

In another example, system includes a light source, at least one processor, and computer-readable memory. The light source can be configured to emit directional light. The computer-readable memory can be encoded with instructions that, when executed by the at least one processor, cause the system to: emit the directional light from the light source through fuel contained in a fuel tank; determine a refraction angle of the directional light after the directional light passes through an interface with the fuel; determine an index of refraction of the fuel based on the measured refraction angle; and determine a density of the fuel based on the determined index of refraction of the fuel.

In another example, a device includes at least one processor and computer-readable memory. The computer-readable memory can be encoded with instructions that, when executed by the at least one processor, cause the device to: determine a refraction angle of directional light emitted from a light source through fuel contained in a fuel tank after the directional light passes through an interface with the fuel; determine an index of refraction of the fuel based on the measured refraction angle; and determine a density of the fuel based on the determined index of refraction of the fuel.

BRIEF DESCRIPTION OF THE DRAWINGS

FIGS. 4A and 4B are diagrams illustrating a wing of an aircraft with no bending, and with some bending, respectively.

FIGS. 5A and 5B are diagrams illustrating a reference image and an active image, respectively, for determining the bend of an aircraft wing.

DETAILED DESCRIPTION

Figure 1:
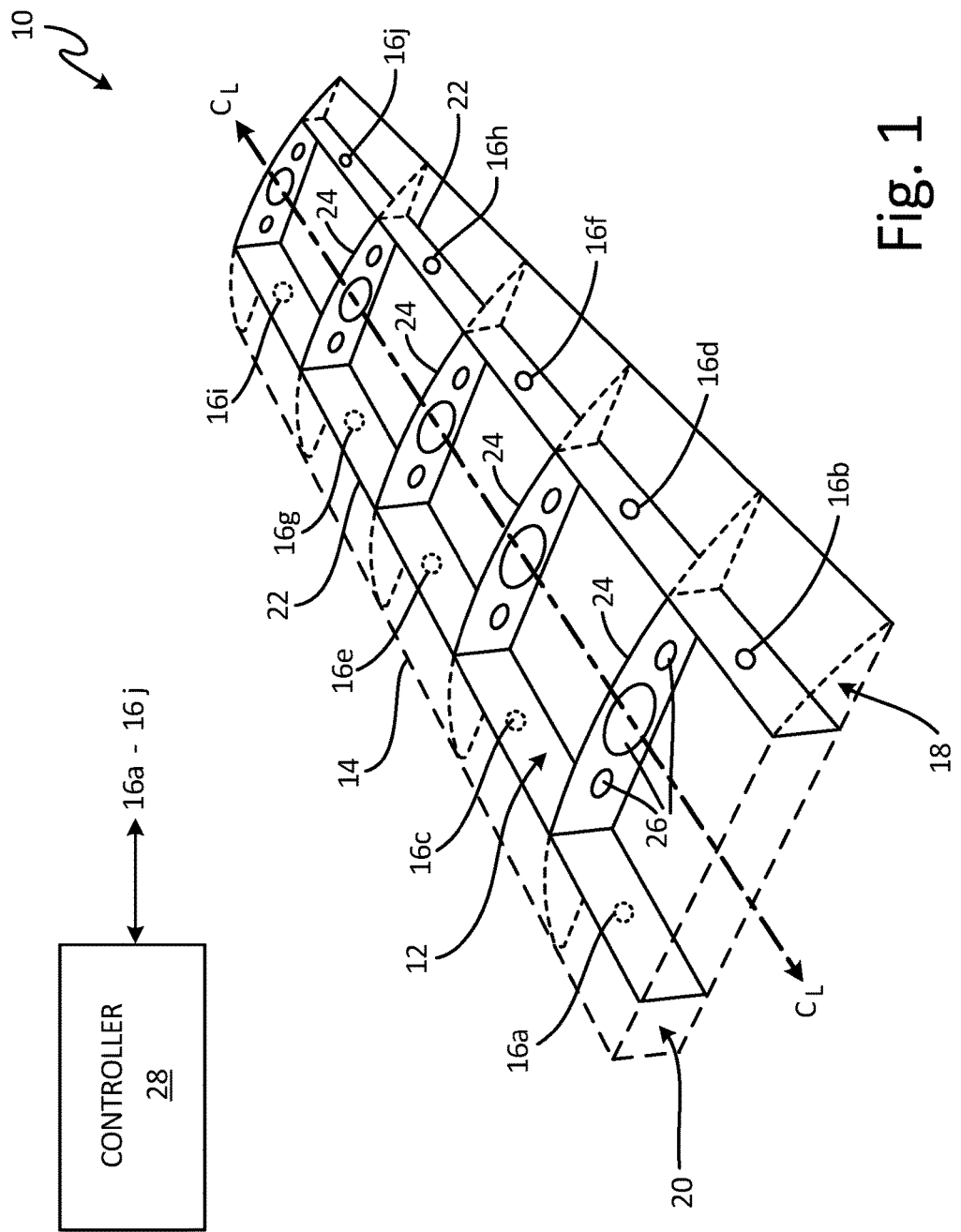
FIG. 1 is a diagram illustrating a fuel tank monitoring system that includes imagers for determining properties of the fuel tank

FIG. 1 is a diagram illustrating fuel tank monitoring system 10, which includes fuel tank 12 disposed within aircraft wing 14. Fuel tank monitoring system 10 includes imagers 16a-16j for determining fluid and/or physical properties of fuel tank 12. Wing 14 is oriented about centerline $C_L$ and includes trailing edge space 18, leading edge space 20, and fuel tank 12. As illustrated in FIG. 1, fuel tank 12 is defined by spars 22, and upper and lower skins of wing 14. Wing 14 includes structural members such as spars 22 and ribs 24, which may be internal or external to fuel tank 12, or may define boundaries of fuel tank 12. Ribs 24 may include structural elements 26, which are illustrated as holes within ribs 24. Fuel tank 12 may include many more structural elements (i.e., physical features) not shown in FIG. 1, which may be in addition to, or part of, spars 22 and ribs 24. While illustrated within wing 14, fuel tank 12 may be any structure designed to hold a fluid.

Fuel tank monitoring system 10 may also include controller 28, which may be operatively connected to provide two-way communication with imagers 16a-16n. Controller 28 may be a microprocessor implemented within a fuel avionics system, for example. In other embodiments, each imager 16a-16j may include its own respective controller in addition to, or in replacement of, controller 28. Controller 28, in some examples, can include one or more processors and computer-readable memory encoded with instructions that, when executed by the one or more processors, cause controller 28 and/or other elements of fuel tank monitoring system 10 to operate in accordance with techniques described herein. Examples of such processors can include any one or more of a microprocessor, a controller, a digital signal processor (DSP), an application specific integrated circuit (ASIC), a field-programmable gate array (FPGA), or other equivalent discrete or integrated logic circuitry.

Computer-readable memory of controller 28 can be configured to store information within controller 28 during operation. Computer-readable memory, in some examples, can be described as a computer-readable storage medium. In some examples, a computer-readable storage medium can include a non-transitory medium. The term "non-transitory" can indicate that the storage medium is not embodied in a carrier wave or a propagated signal. In certain examples, a non-transitory storage medium can store data that can, over time, change (e.g., in RAM or cache). In some examples, computer-readable memory of controller 28 can include temporary memory, meaning that a primary purpose of the computer-readable memory is not long-term storage. Computer-readable memory of controller 28, in some examples, can be described as a volatile memory, meaning that the computer-readable memory does not maintain stored contents when electrical power to controller 28 is removed. Examples of volatile memories can include random access memories (RAM), dynamic random access memories (DRAM), static random access memories (SRAM), and other forms of volatile memories. In some examples, computer-readable memory can be used to store program instructions for execution by one or more processors of controller 28. For instance, computer-readable memory of controller 28 can be used by software or applications executed by controller 28 to temporarily store information during program execution.

Imagers 16a-16j may be any image capture devices capable of producing an analog or digital image from received light at one or more wavelengths. Imagers 16a-16j may be, for example, cameras, short-wave infrared imagers, thermal imagers, fiber optic bundles, or any other device capable of capturing light to form an image. While illustrated as located on external surfaces of fuel tank 12, imagers 16a-16j may be implemented anywhere internal or external to fuel tank 12. Imagers 16a-16j may be located in positions so as to obtain a complete two-dimensional and/or three-dimensional representation of fuel tank 12, or may be implemented to only obtain images of desired locations of fuel tank 12. For example, fewer imagers 16a-16j may be implemented in fuel tank 12, and the portions of tank 12 that are not captured in any field of view of imagers 16a-16j may be inferred based upon the known structure of fuel tank 12.

Imagers 16a-16j may provide image data to controller 28 to determine properties of fuel tank 12. Image data may be obtained using any device capable of producing electronic data based upon incoming light such as, for example, a focal-plane array. The properties of fuel tank 12 may include, but are not limited to, physical features of an interior of fuel tank 12 (e.g., locations and/or physical contours of spars 22, ribs 24, structural elements 26, or other physical features of the interior of fuel tank 12), a level and/or volume of fuel within the interior of fuel tank 12, tilt of an aircraft that includes fuel tank 12, an amount of bend of wing 14 of the aircraft, a density of the fuel within fuel tank 12, a chemical composition of fluids within fuel tank 12 (e.g., fuel, gases within an ullage of fuel tank 12, or other fluids within fuel tank 12), and/or a temperature of fluid(s) within fuel tank 12. To obtain these properties, processing may be performed on the image data obtained by imagers 16a-16j. The focal-plane array or other image sensing device of imagers 16a-16j may be configured to output an array of pixels, for example. The array of pixels may be provided to a local controller of imager 16a-16j, or controller 28, for processing. Controller 28 can utilize the determined properties of fuel tank 12 to produce a fuel measurement value representing an amount of fuel contained in fuel tank 12. The fuel measurement value can include, for example, a volume of fuel, a mass of fuel (e.g., based on a volume and density of the fuel), or other fuel measurement values representing an amount of fuel contained in fuel tank 12. Controller 28 can output an indication of the fuel measurement value, such as by outputting data specifying the fuel measurement value via a communications data bus or other network (not illustrated), a visual indicator (e.g., a graphical gauge, a warning light, or other visual indicator) of the fuel measurement value, or other indication of the fuel measurement value.

By utilizing imagers 16a-16j to determine properties of fuel tank 12, prior art capacitive probes may be eliminated (or a number of capacitive probes reduced) from fuel tank 12, which removes or reduces the electromagnetic fields generated by the capacitive probes. In examples where imagers 16a-16j are implemented external to fuel tank 12, obtaining a field of view through, for example, a window, all electronic components used for fuel volume determinations may be removed from fuel tank 12. Further, many or all of the electronics for imagers 16a-16j may be contained within leading edge space 20 and trailing edge space 18, regardless of the imagers' locations inside or outside of fuel tank 12. This can reduce the need for opening fuel tank 12 to provide service for imagers 16a-16j. Imagers 16a-16j may also be utilized to perform inspections of the internals of fuel tank 12, further reducing the need for entry into fuel tank 12. For example, image data obtained by imagers 16a-16j may be utilized to perform routine inspections for corrosion, cracks or other maintenance needs within fuel tank 12.

Figure 2A:
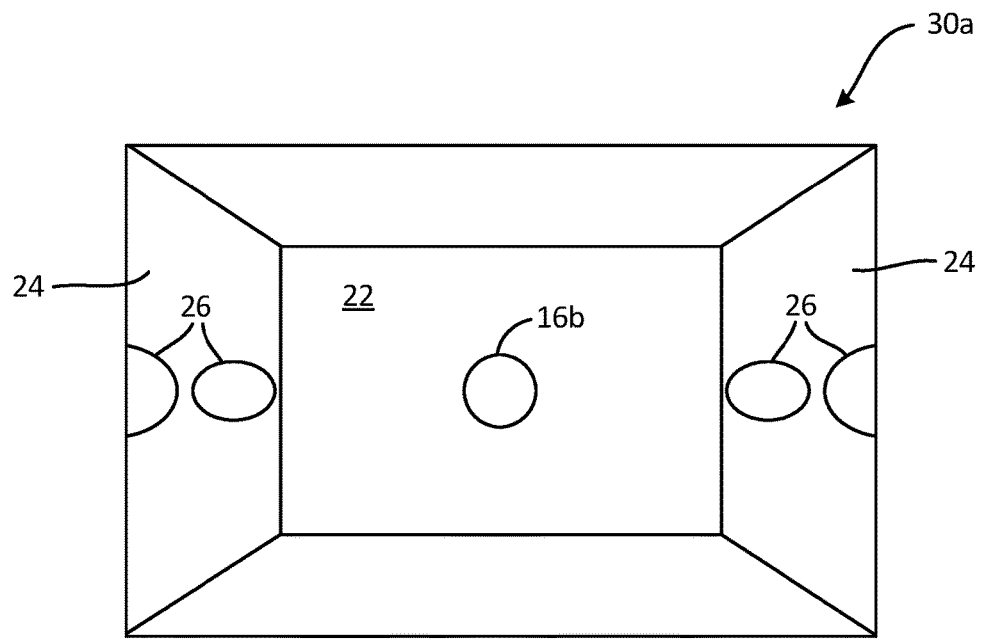
FIGS. 2A and 2B are diagrams illustrating a reference image and an active image, respectively, for a fuel tank monitoring system.
Figure 2B:
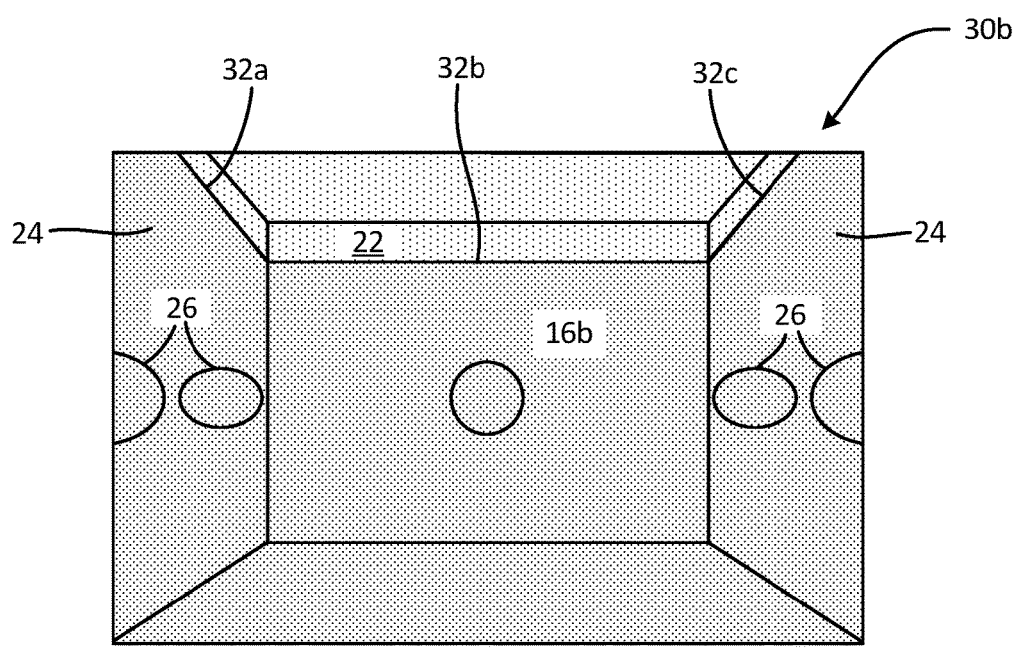

FIGS. 2A and 2B are example images 30a and 30b captured by imager 16a. While illustrated as images 30a and 30b captured by imager 16a, images 30a and 30b may be captured by any imager 16a-16j implemented for fuel tank 12. Moreover, it should be understood that in some examples, techniques described herein can utilize more than the two images 30a and 30b described with respect to the example of FIGS. 2A and 2B. FIG. 2A illustrates reference image 30a which may be a reference for the field of view of imager 16a. Reference image 30a may be taken at any reference time for fuel tank 12. For example, and as illustrated in FIG. 2A, reference image 30a may be obtained by imager 16a during a time in which fuel tank 12 does not contain any fuel. In other examples, reference image 30a can be obtained by imager 16a during a time when fuel tank 12 contains fuel. Reference image 30a may also be obtained while the aircraft is on the ground when fuel tank 12 is at or near empty to help ensure that there is minimal wing bending, which may affect the orientation of physical features within fuel tank 12. While illustrated as a reference image obtained while on the ground with minimal fuel in fuel tank 12, reference image 30a may be obtained at any other time, such as when the aircraft is in air and/or when fuel tank 12 contains fuel.

FIG. 2B illustrates active image 30b which may be actively obtained during operation of fuel tank monitoring system 10 and/or the aircraft for which fuel tank monitoring system 10 is implemented. Active image 30b depicts an instance in which fuel is present within fuel tank 12. Fuel level lines 32a-32c are illustrated to depict a level of fuel on each surface of fuel tank 12 that is in the field of view of imager 16a. Fuel level lines 32a-32c represent an interface between fuel and ullage (i.e., an unfilled space of fuel tank 12 that can be occupied by one or more gases). Active image 30b may be obtained using the same imager 16a-16j that was used to obtain reference image 30a. Therefore, images 30a and 30b may be processed by controller 28 to determine at least the level of fuel in fuel tank 12.

Image processing may be performed by controller 28, for example, to determine the location of fuel level lines 32a-32c. This image processing may include feature recognition, edge detection, or any other type of image recognition.

Feature recognition, for example, may perform an image-to-image overlay to compare active image 30b to reference image 30a in order to determine locations of the interior of fuel tank 12 where images 30a and 30b do not match. Controller 28 may detect disconnects from the overlay to determine where fuel level lines 32a-32c are located.

Edge detection may also be utilized to detect fuel level lines 32a-32c. Edge detection may be performed by searching active image 30b for sharp changes in light intensity. For example, if image 30b includes an array of pixels, controller 28 may search the pixel array to detect adjacent pixels that have a significant difference in intensity. Once controller 28 detects edges within fuel tank 12, a comparison may be made to the known structure in the field of view of imager 16a to determine if the edges are indicative of the fuel interface. For instance, controller 28 can store a model of a shape of fuel tank 12, such as a model defined using computer aided design (CAD) technologies that includes relative locations of physical features of the shape of fuel tank 12, including physical features corresponding to external boundaries of, and internal physical features of, the interior of fuel tank 12 (e.g., spars 22, ribs 24, structural elements 26, or other physical features of the interior of fuel tank 12). In addition to feature and edge detection, any other image processing techniques, such as the use of machine learning techniques (e.g., artificial neural networks, Bayesian networks, support vector machines, or other types of machine learning techniques), may be utilized to process active images 30b to determine a location and/or intersection of fuel level lines 32a-32c with physical features of the interior of fuel tank 12.

As illustrated in FIG. 2B, three fuel level lines 32a-32c may be determined from the field of view of imager 16a. Active images from other imagers 16b-16j may also be utilized to determine fuel level lines for each wall of fuel tank 12, for example. If locations of fuel level lines are determined for each wall of fuel tank 12, the volume of fuel may be determined. For instance, controller 28 can compare one or more locations of the interior of fuel tank 12 corresponding to the determined fuel level lines that correspond to (e.g., intersect) locations of one or more physical features of the interior of fuel tank 12 (e.g., determined based on reference image 30a, a model of the shape of fuel tank 12, or combinations thereof). Controller 28 can determine, in some examples, an amount of fuel that is between the determined fuel level lines and a bottom of fuel tank 12 (i.e., bottom of fuel tank 12 as defined with respect to level flight of the aircraft). The tilt of the aircraft, for example, may also be determined by knowing the fuel level lines for each wall of fuel tank 12. For example, if fuel level line 32a of image 30b is higher than fuel level line 32c, controller 28 may be able to determine a tilt of the aircraft based on fuel level lines 32a-32c and the known geometry of fuel tank 12 (e.g., known via the model of the shape of fuel tank 12).

Figure 3:
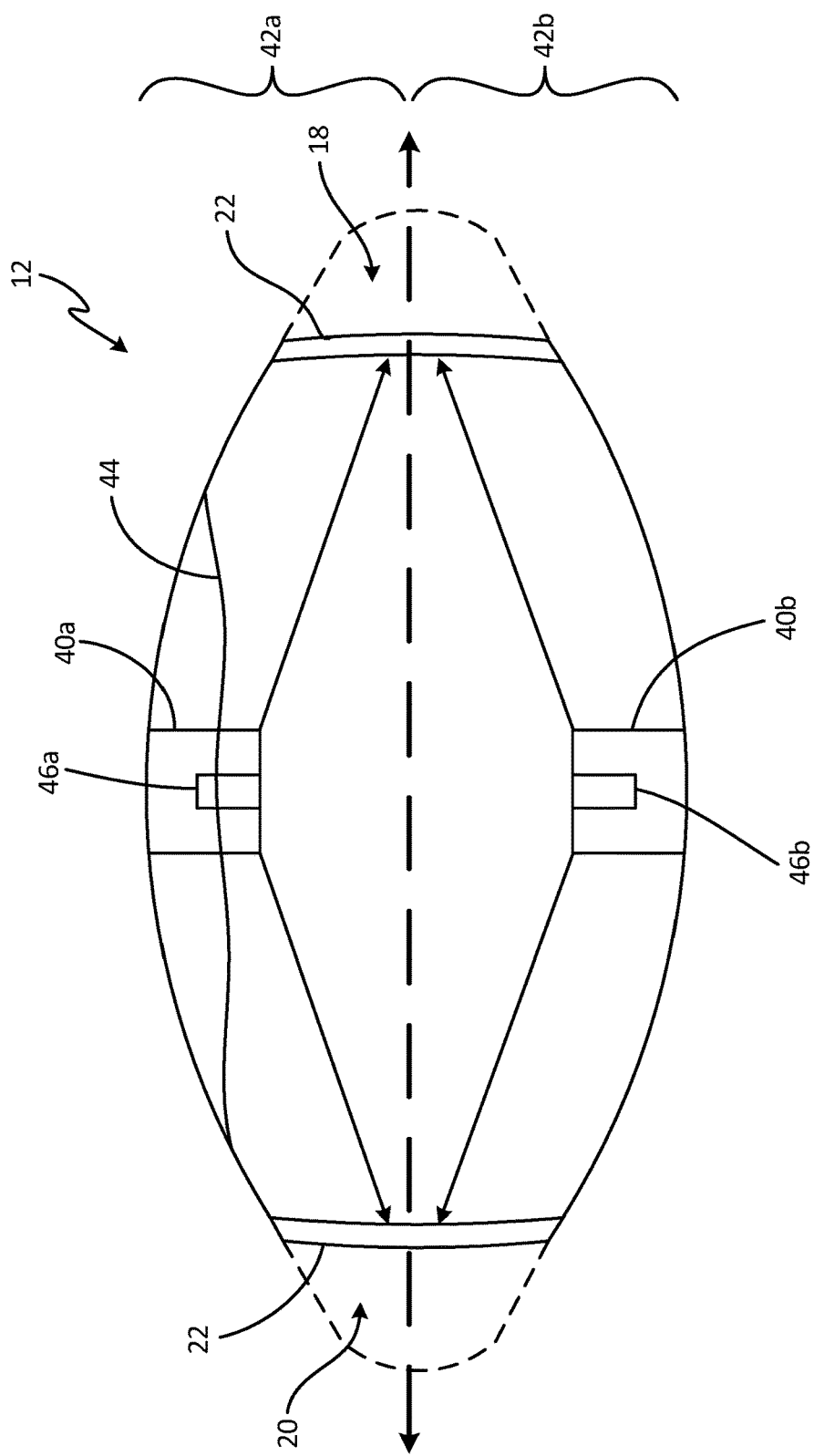
FIG. 3 is a diagram illustrating a fuel tank that includes imagers having opposing fields of view.

FIG. 3 is a diagram that illustrates fuel tank 12 including imagers 40a and 40b. Imagers 40a and 40b are capable of viewing top portion 42a and bottom portion 42b of fuel tank 12, respectively, to detect a fuel interface 44. Imagers 40a and 40b may include light sources 46a and 46b, respectively. While illustrated in FIG. 3 as located inside fuel tank 12, imagers 40a and 40b may also be located outside of fuel tank 12 while still having a view of the inside structure of fuel tank 12 through a window, for example. The field of view for each imager 40a and 40b is illustrated by the arrows in FIG. 3.

Imager 40a may be located proximate to (e.g., attached to or otherwise disposed proximate to) the top skin of wing 14, which may also be the top boundary of fuel tank 12 in some examples. Imager 40a may therefore have a field of view that is capable of imaging bottom portion 42b of fuel tank 12. Imager 40b may be located proximate to (e.g., attached to or otherwise disposed proximate to) the bottom skin of wing 14, which may also be the bottom boundary of fuel tank 12 in some examples. Imager 42a may therefore have a field of view that is capable of imaging top portion 42a of fuel tank 12. Light sources 46a and 46b may be implemented to illuminate the internal structure of fuel tank 12. Light sources 46a and 46b may be any devices capable of emitting light at any desired wavelength or range of wavelengths such as, for example, a laser, a light-emitting diode (LED), or any other light emitter.

Imager 40a may be submerged below fuel interface 44, for example. In examples where imager 40a is submerged and the field of view of imager 40a originates beneath the top surface of the fuel, controller 28 may not be able to detect fuel interface 44 within fuel tank 12 based on an image from imager 40a. However, in such examples, imager 40b that is located with a field of view of upper portion 42a can enable controller 28 to detect fuel interface 44 based upon an image from imager 40b. Detection of fuel interface 44 may be accomplished using any type of image processing techniques capable of detecting fuel interface 44 from electronic data obtained by imagers 40a and 40b, such as the techniques discussed above. For example, an image-to-image overlay may be used to determine a location and/or intersection of fuel level lines with physical features of the interior of tank 12 to determine a location of fuel interface 44. In other embodiments, imager 40a may be implemented outside fuel tank 12 such that imager 40a is never submerged below fuel interface 44 and therefore, imager 40b is not required to determine the location of fuel interface 44.

During other operational states, fuel interface 44 may be below the field of view of imager 40b. In such operational states, imager 40a, located with a field of view that includes lower portion 42b, can enable controller 28 to detect fuel interface 44 even though it is below the level of imager 40b. Hence, all possible locations of fuel boundary 44 may be detected within fuel tank 12 utilizing imagers 40a and 40b.

Light sources 46a and 46b may be controlled in any desirable manner to illuminate fuel tank 12 for imagers 40a and 40b. Although illustrated as integral to imagers 40a and 40b, light sources 46a and 46b may also be implemented as devices separate from imagers 40a and 40b. Because imagers 40a and 40b produce image data based upon collected light, it may be desirable to control an intensity, and direction, of light within fuel tank 12. For example, light source 46a can be turned on to provide reflective light for detecting fuel interface 44 by imager 40a and/or transmissive light for detecting fuel interface 44 by imager 40b. Light source 46b can be turned on to provide transmissive light for detecting fuel interface 44 by imager 40a and reflective light for detecting fuel interface 44 by imager 40b. In other embodiments, both light sources 46a and 46b may be turned on for detection of fuel interface 44 by one or more of imagers 40a and 40b. Similar operation of light sources 46a and 46b may be performed for any other imager implemented within fuel tank 12.

FIG. 4A illustrates wing 14 with no bending, and FIG. 4B illustrates wing 14 with bending. Wing 14 includes imager 50 disposed therein, and also includes structural elements 52a-52d (i.e. physical features of the interior of fuel tank 12). Imager 50 may be any type of image capture device, including any of those discussed in previous embodiments.

Imager 50 may have a field of view illustrated by the arrows extending from imager 50 in FIGS. 4A and 4B. This field of view may be such that imager 50 is able to obtain image data that includes all of structural elements 52a-52d relative to one another. With no bend, wing 14 remains oriented about centerline $C_L$. With bending, the tip of wing 14 is displaced below centerline $C_L$ and is oriented about a bend line $C_B$. The angle $\theta_B$ is the angle between centerline $C_L$ and bend line $C_B$. While illustrated as bending downward, which may occur during refueling of an aircraft on the ground, for example, wing 14 may also bend upward during flight.

Wing bending may be important in determining a level of fuel within fuel tank 12 because the orientation of fuel within fuel tank 12 may be altered due to bending in wing 14. In addition to determination of fuel levels, a determination of wing bending of wing 14 may be useful for other systems of an aircraft. Because imager 50 may be utilized to detect wing bending in addition to detecting fuel levels as described in the previous embodiments, no extra systems need to be implemented on the aircraft to detect wing bending.

FIG. 5A illustrates an example reference image 53a obtained by imager 50 while wing 14 has no bend (e.g., for the embodiment illustrated in FIG. 4A), and FIG. 5B illustrates an active image 53b obtained by imager 50 while wing 14 has a bend of $\theta_B$ (e.g., for the embodiment illustrated in FIG. 4B). While illustrated as holes within structural elements 52a-52d, any other structural members may be compared to one another to determine an amount of wing bending $\theta_B$. While illustrated as ribs of wing 14, structural elements 52a-52d may be any structural elements within wing 14 that may be viewed relative to one another. In addition, while illustrated as located to have a field of view that extends generally in a direction from a root to a tip of wing 14, imager 50 (or any one or more additional imagers) can be located to have a field of view of any portion of the interior of fuel tank 12, such that controller 28 can determine an amount of wing bending of wing 14 based on relative displacement of physical features of the interior of fuel tank 12 based on the generated image data from the one or more imagers, as is further described below.

Images 53a and 53b include distances 54a-54c. Distance 54a is the distance between the bottom edge of the hole in structural element 52a and the bottom edge of the hole in structural element 52b. Distance 54b is the distance between the bottom edge of the hole in structural element 52b and the bottom edge of the hole in structural element 52c. Distance 54c is the distance between the bottom edge of the hole in structural element 52c and the bottom edge of the hole in structural element 52d. While illustrated as three distances 54a-54c, any number of comparisons between structural elements of wing 14 may be utilized to achieve a desired accuracy of the detected wing bending.

The angle $\theta_B$, illustrated in FIG. 4B, may be determined by comparing distances 54a-54c of image 53b, with distances 54a-54c of image 53a to determine a relative displacement between structural elements 52a-52d that can correspond to an amount of wing bending of wing 14. Controller 28, or any other controller, may accomplish this by using any form of image processing, such as those discussed above. Image 53b may be compared to image 53a using an image-to-image overlay, for example, and the difference between distances 54a-54c of images 53b and 53a may be determined. In another embodiment, if the base distances 54a-54c are known (e.g., via a model of a shape of fuel tank 12 that specifies relative locations of physical features of the interior of fuel tank 12), other forms of image processing may be utilized to determine distances 54a-54c of image 53b, and those distances 54a-54c may be compared to the base values to determine an amount of wing bending $\theta_B$. While the embodiment discussed with reference to FIGS. 4A-5B may be utilized to detect a single angle $\theta_B$, the techniques described herein may be applied to detect higher-dimensional properties of wing bending by using, for example, three-dimensional modeling of wing 14 based on images obtained from imagers positioned within wing 14.

Controller 28 can utilize the determined amount of wing bending $\theta_B$ to determine a fuel measurement value representing an amount of fuel contained in fuel tank 12, such as a fuel volume, a fuel mass, or other fuel measurement values representing an amount of fuel contained in fuel tank 12. For instance, controller 28 can store and/or determine a model of a shape of fuel tank 12, such as a model defined by CAD or other techniques that specified relative locations of physical features of the interior of fuel tank 12. Controller 28 can determine the fuel measurement value based on the determined amount of wing bending $\theta_B$, such as by modifying the shape of fuel tank 12 using the model of the shape of fuel tank 12 and determining the fuel measurement value based on the modified shape. For instance, controller 28 can modify the locations of physical features of the interior of fuel tank 12 within the model based on the determined amount of wing bending $\theta_B$. Controller 28 can determine the fuel measurement value representing the amount of fuel contained in fuel tank 12 based on the a location of fuel and ullage (e.g., associated with one or more of fuel level lines 32a-32c, or more fuel level lines) corresponding to (e.g., intersecting) locations of one or more of the physical features of the interior of fuel tank 12 defined using the modified shape within the model.

Figure 6:
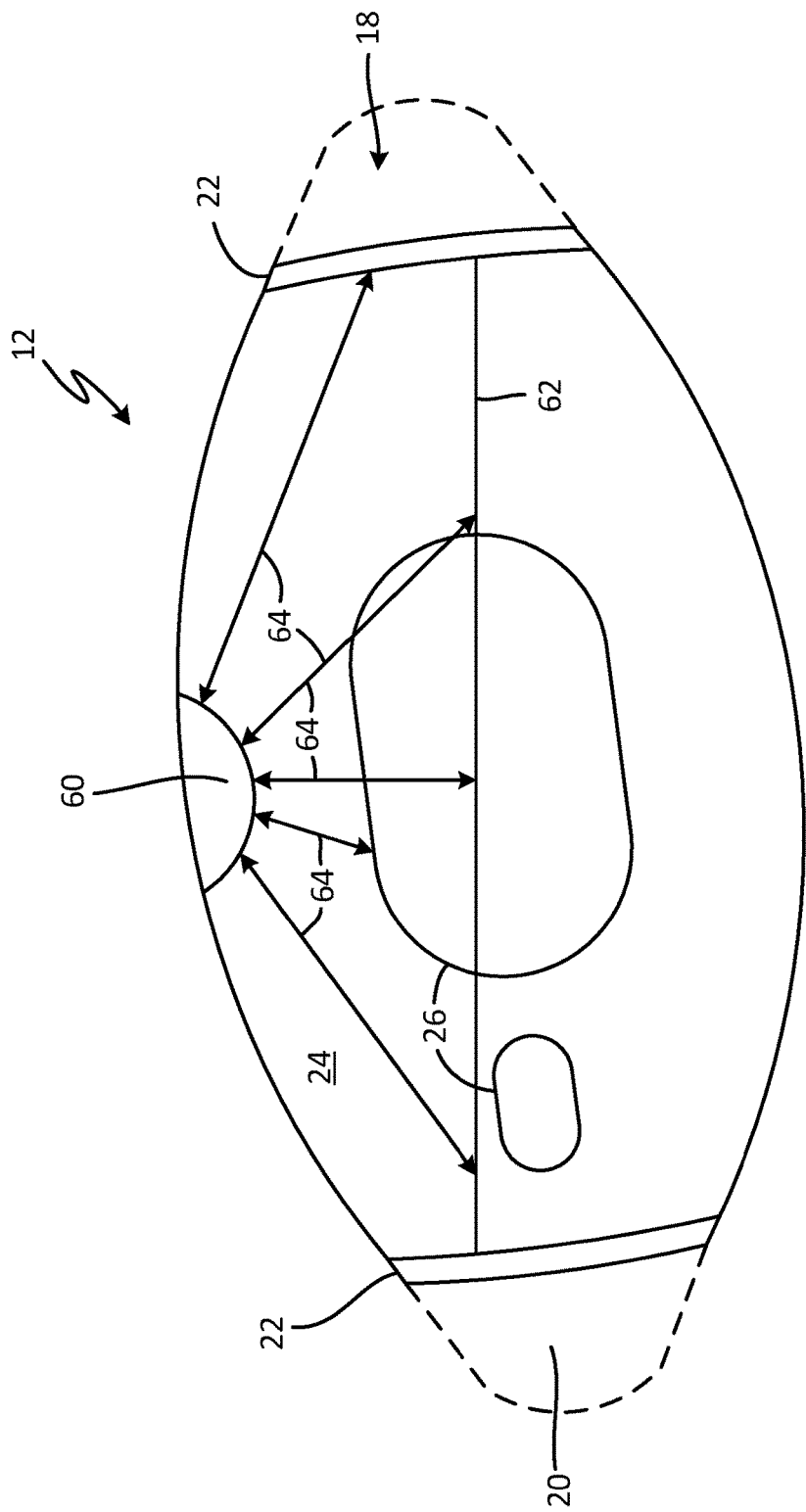
FIG. 6 is a diagram illustrating a fuel tank that includes a lidar imager for determining properties of the fuel tank.

FIG. 6 is a diagram illustrating fuel tank 12 that includes time-of-flight imager 60. Time-of-flight imager 60 may be implemented as a Light Detection and Ranging (lidar) device or any other image capture device capable of measuring a time-of-flight of reflected light. Time-of-flight imager 60 may emit light 64 outward from time-of-flight imager 60 using a built-in, or separate, directional light source as illustrated by the arrows in FIG. 6. Light 64 may be emitted utilizing a laser, or any other light source capable of emitting light at a known wavelength. Lasers provide a directed light source that can be emitted toward fuel interface 62. Light 64 is reflected off of fuel interface 62 and may be obtained and analyzed by controller 28, for example. As illustrated in FIG. 6, other features, such as spars 22 and structural features 26 may also be detected by time-of-flight imager 60 based upon reflected light.

Time-of-flight imager 60 may include a focal plane array, for example, that provides an image on a pixel-by-pixel basis. For each pixel, a time-of-flight may be determined based upon a known time of sending out light 64 by the laser or other light source of time-of-flight imager 60. Any type of time-of-flight detection may be utilized such as, for example, range gating or direct time-of-flight to provide an indication of time-of-flight for each pixel. For example, for range gating, the time-of-flight may be indicated based upon an intensity of the pixel, whereas for direct time-of-flight, the actual time-of-flight for the light to travel from the light source and back to the imager is measured for each pixel.

In another embodiment, the phase of the reflected light 64 may be used by time-of-flight imager 60 to determine, on a pixel-by-pixel basis, the time-of-flight for light 64 to travel from the light source back to imager 60. For example, when light is reflected off of an interface, such as fuel interface 62, the phase of the light is shifted based upon the distance the light traveled prior to reflection. Therefore, the phase of light for each pixel may be utilized to determine a time-of-flight for each pixel.

By knowing the time-of-flight for each pixel obtained by the imager of time-of-flight imager 60, a three-dimensional image of fuel tank 12 may be determined (e.g., by controller 28). Controller 28, utilizing the generated three-dimensional image data, can determine three-dimensional properties of fuel tank 12, such as a location of physical features of the interior of fuel tank 12, a location of fuel interface 62 (i.e., representing an interface between fuel and ullage of fuel tank 12), a location of fuel interface 62 corresponding to (e.g., intersecting) the physical features of the interior of fuel tank 12, a tilt of the aircraft including fuel tank 12, a bending of wing 14 including fuel tank 12 (e.g., based on a relative displacement of the identified physical features of the interior of the fuel tank 12 as compared to a model of the shape of fuel tank 12), or other three-dimensional properties of fuel tank 12. Such three-dimensional data can enable controller 28 to determine a fuel measurement value corresponding to an amount of fuel contained in fuel tank 12 without comparison to or generation of reference images of the interior of fuel tank 12. For example, fuel interface 62 is illustrated in FIG. 6 with tilt, indicating that the aircraft carrying fuel tank 12 is tilted with respect to the local acceleration vector of the aircraft. By generating a three-dimensional image of fuel tank 12, the tilt of fuel interface 62 may be determined with great precision. While illustrated internal to fuel tank 12, time-of-flight imager 60 may be implemented anywhere in which it is possible to get an internal image of fuel tank 12, such as external to fuel tank 12 through a window, for example. Time-of-flight imager 60 may also be utilized in any of the previous embodiments disclosed to detect fuel levels, wing bending, tilt, or any other properties of fuel tank 12.

In addition to time-of-flight imaging, any of the imagers illustrated in FIGS. 1-6 may be configured to determine a fuel interface or other property of a fuel tank based on a pattern of light. For example, instead of a lidar device that measures time of flight from one or more light pulses, imager 60 of FIG. 6 may be configured to project a pattern of light in fuel tank 12. This pattern may be, for example, several beams of light projected in different, but known, directions. All beams may be configured to hit fuel interface 62 regardless of the level of fuel in fuel tank 12. Because the beams are projected in different directions from the light source of imager 60, the pattern will change based on the location and orientation of fuel interface 62 relative to imager 60. For example, if three light beams are emitted from the light source of imager 60, then three points on fuel interface 62 will reflect back to imager 60. Imager 60 may produce an image that illustrates the three reflected points. Using the three reflected points, as well as the known direction of the beams from imager 60, a location and orientation of fuel interface 62 may be determined.

Figure 7:
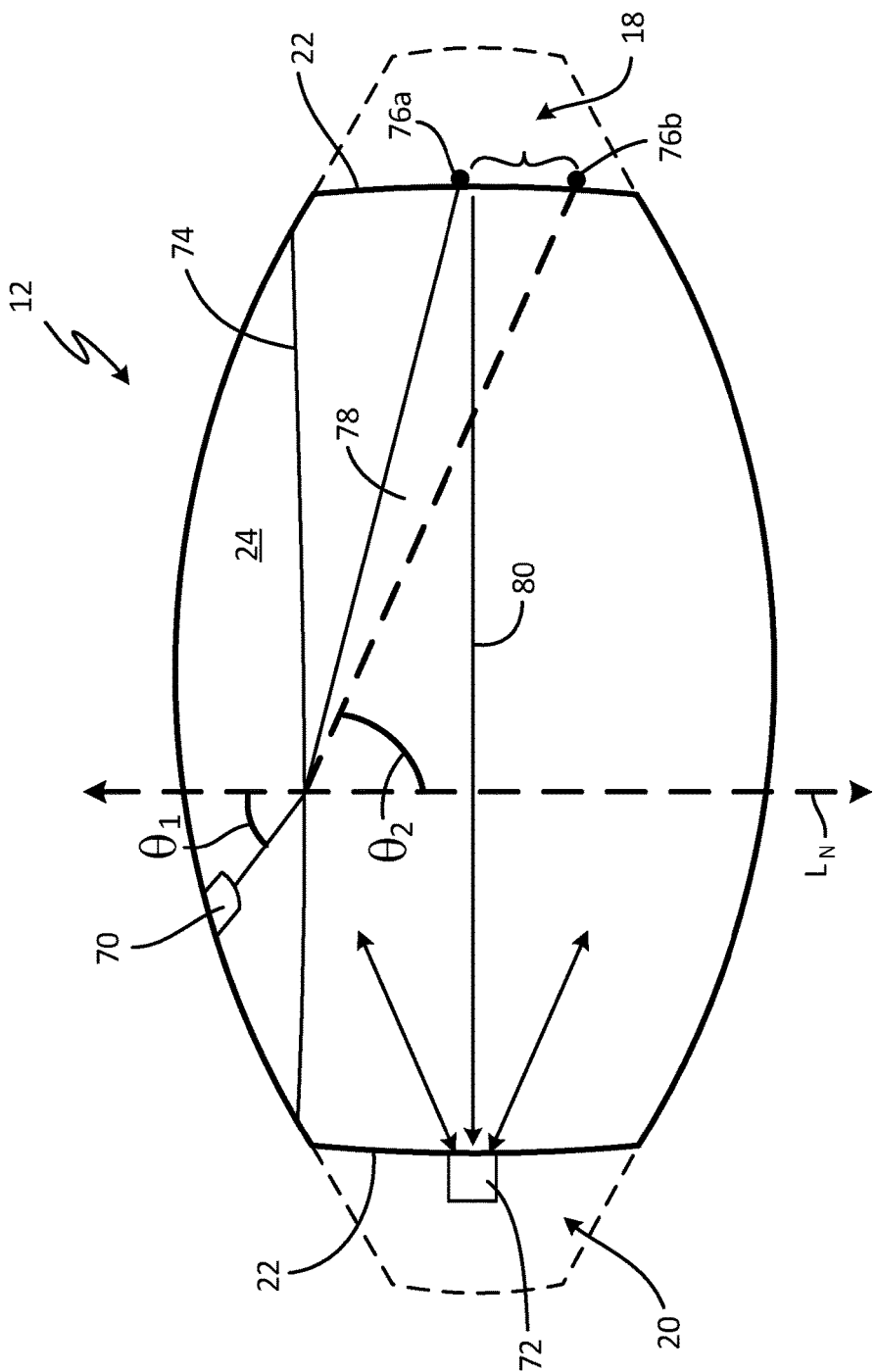
FIG. 7 is a diagram illustrating a fuel tank that includes an imager for determining a density of fuel within the fuel tank.

FIG. 7 is a diagram illustrating fuel tank 12 that includes light source 70 and imager 72 utilized to determine a density of fluid (e.g., fuel) within fuel tank 12. Imager 72 may be any image capture device such as those discussed in the above embodiments. Light source 70 may be any light source, such as any of those discussed in the above embodiments. While illustrated as external to fuel tank 12 in wing space 20, imager 72 may be located at different positions external to or internal to fuel tank 12.

Refraction of the light emitted from light source 70 after the light passes through an interface with fuel contained in fuel tank 12 may be utilized to determine a density of the fuel within fuel tank 12. For instance, as in the example of FIG. 7, the interface with the fuel contained in fuel tank 12 can be an interface between the fuel and gas within an ullage of fuel tank 12. In other examples, such as when light source 70 is located at a position that may typically be submerged below a level of fuel contained in fuel tank 12, the interface with the fuel contained in fuel tank 12 can include an interface between, e.g., a window separating light source 70 and fuel contained in fuel tank 12.

As illustrated in FIG. 7, a directed beam of light 78 emitted by light source 70 may be aimed at one of spars 22, or any other structural element of fuel tank 12, for example. Location 76a may be the location of the interior of fuel tank 12 that beam 78 hits (i.e., intersects) after traveling through fuel interface 74. Location 76b may be a location of the interior of fuel tank 12 corresponding to non-refraction of beam 78, such as the location that beam 78 hits (i.e., intersects) after traveling through fuel tank 12 when fuel tank 12 is empty of fuel (illustrated by the dashed line in FIG. 7). Angle $\theta_1$ is the angle of beam 78 above fuel interface 74 relative to normal $L_N$. Angle $\theta_2$, which can be considered a refraction angle of beam 78 after beam 78 passes through the interface with the fuel (fuel interface 74 in this example), is the angle of beam 78 relative to normal $L_N$ below fuel interface 74. Angle $\theta_1$ may be known based on the installed location and directional orientation of light source 70. If the level of fuel interface 74 is also known, the distance $D_1$ may be utilized to determine angle $\theta_2$. This may be advantageous when measuring the density of fuel, for example, prior to takeoff when the level of fuel interface 74 is known.

Imager 72 may be implemented to receive reflected light 80 to determine position 76a. Position 76a may be determined by controller 28, for example, using image processing techniques, such as those discussed in the above embodiments. Location 76b may be a known reference location indicative of non-refraction of beam 78, such as the location of the interior of fuel tank 12 that beam 78 hits when there is no fuel in tank 12. By comparing the determined location 76a obtained from the image data to the reference location 76b, distance $D_1$ may be calculated. For example, controller 28 may process an image-to-image overlay of a first image that includes the detected location 76a, and a reference image that includes reference location 76b to determine a distance between locations 76a and 76b within the overlay. Using a model of the internals of tank 12, for example, the determined distance within the overlay may then be correlated to the actual physical distance $D_1$. Using distance $D_1$, and the known level of fuel interface 74, $\theta_2$ may be determined by controller 28. Using both $\theta_1$ and $\theta_2$, controller 28 can utilize Snell's law to determine the refractive index of the fuel. After obtaining the refractive index, known properties of the fuel within fuel tank 12, along with a sensed temperature of the fuel, may be utilized to calculate the density of the fuel based on the refractive index.

To calculate the density from the refractive index, the temperature of the fuel must be known, as temperature is also a variable that affects refractive index. To obtain temperature, a temperature probe (not shown) may be implemented to sense the temperature of the fuel. In another embodiment, imager 72 may be implemented, for example, as a far infrared imager, or any other thermal imager, to detect blackbody radiation. A far infrared imager, for example, may produce electronic data indicative of temperature in its field of view. Each pixel, for example, may have an intensity that is directly proportional to the temperature of the objects within the image. A thermal imager is also capable of receiving the radiation of beam 80 to determine location 76a. This way, both the angle of refraction and the temperature, and thus the density of fuel, may be obtained using a single imager 72. Although described in the present embodiment for imager 72, a thermal imager may be implemented in any of the above embodiments to both obtain images of fuel tank 12 as well as determine the temperature of the contents of fuel tank 12.

Controller 28 can determine a fuel measurement value representing an amount of fuel contained in fuel tank 12 based on the determined density of the fuel. For instance, controller 28 can determine a fuel measurement value representing a mass of fuel contained in fuel tank 12 based on the determined density and a determined volume of the fuel contained in fuel tank 12. Accordingly, techniques described herein can enable a density of fuel contained within fuel tank 12 using imaging techniques, thereby enabling fuel measurement values, such as a mass of fuel contained in fuel tank 12, to be determined.

Figure 8A:
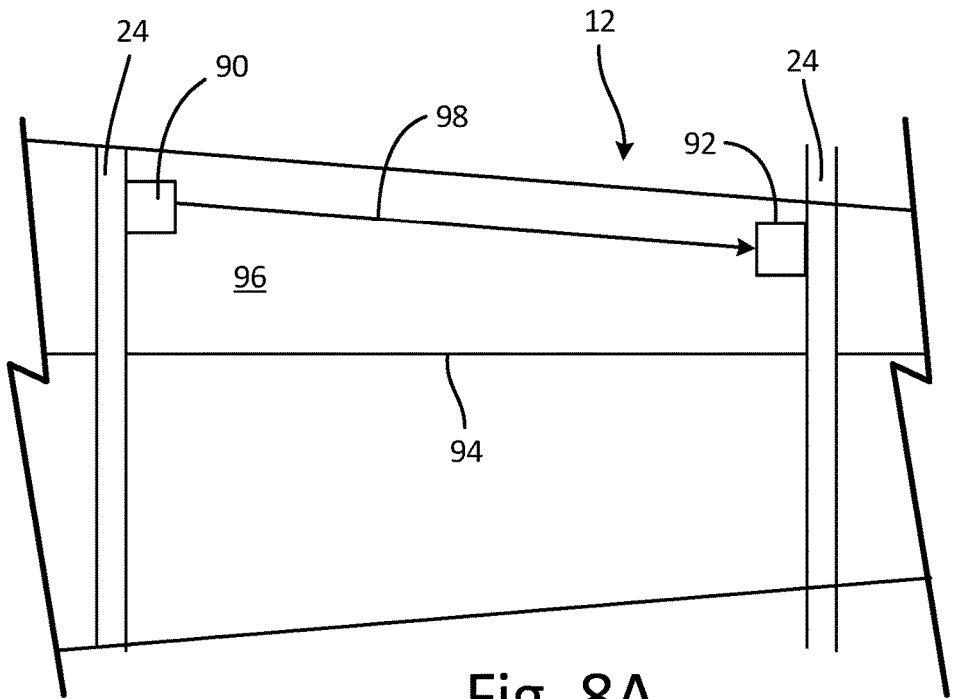
FIGS. 8A and 8B are diagrams illustrating a fuel tank that includes imagers for detecting properties of the ullage gasses within the fuel tank.
Figure 8B:
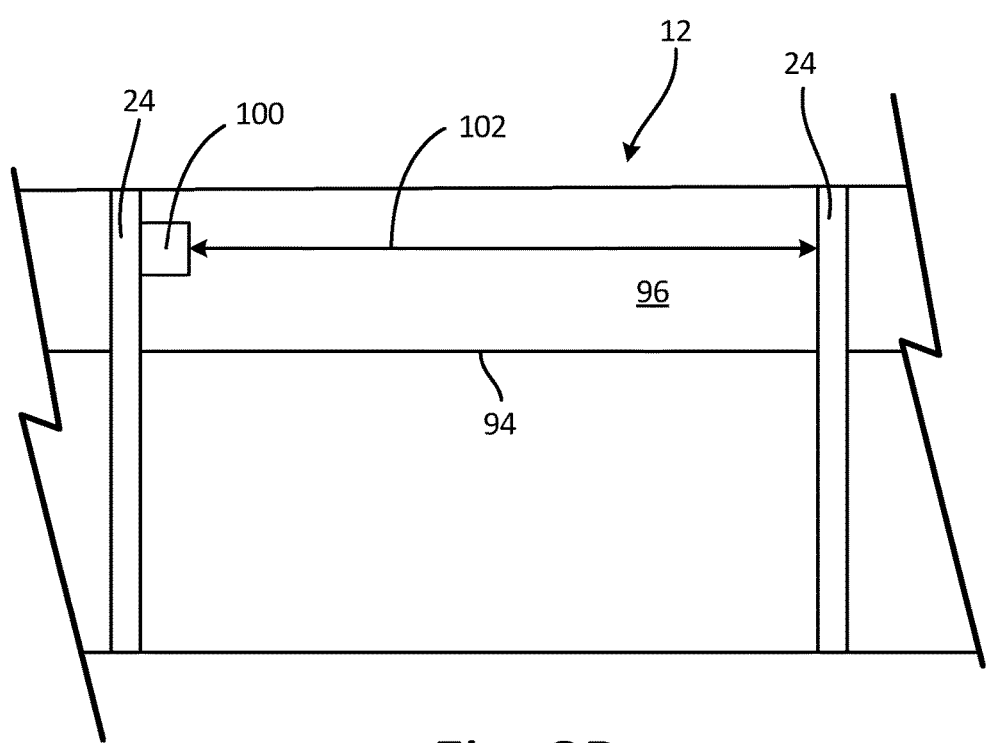

FIGS. 8A and 8B are diagrams illustrating imagers 92 and 100, respectively, implemented to determine properties of ullage gases 96. FIG. 8A illustrates fuel tank 12 that includes light source 90 and imager 92. Fuel interface 94 separates the fuel in tank 12 from ullage gases 96. Light source 90, which may be any light source such as those described in the above embodiments, may be configured to produce directional light beam 98 for receipt by imager 92. FIG. 8B illustrates an imager 100 that includes a local light source, which produces light beam 102 that is directed at the opposing spar 24 and reflected back for receipt by imager 100. In each of the embodiments illustrated in FIGS. 8A and 8B, imagers 92 and 100 may be utilized to determine the absorption of at least one wavelength of beams 98 and 102, respectively.

Absorption of light is dependent upon the medium through which the light travels. Therefore, if beams 98 and 102 remain solely within ullage gases 96, properties of ullage gases 96 may be determined by controller 28, for example, based on the amount of absorption of at least one wavelength of beams 98 and 102. Aircraft systems may include inert gas generating systems configured to produce oxygen-depleted air for the fuel tank ullage to reduce the probability of combustion within the fuel tank. In particular, it is desirable to ensure that oxygen levels remain below a threshold percentage of ullage gases 96. In the example of FIGS. 8A and 8B, fuel tank monitoring system 10 can include and/or be operatively coupled to such an inert gas generating system the produces oxygen-depleted ullage gases 96 (e.g., comprised of, e.g., nitrogen gas or other inert gas).

While it is possible to determine any chemical properties of ullage gases 96, in some examples it may be desirable to determine the presence and/or amount of oxygen within ullage gases 96. In other examples, an amount of inert gas present within ullage gases 96 can be determined. Oxygen, for example, includes a series of absorbing bands and thus, the wavelengths of light beams 98 and 102 can be selected to be within the absorbing bands of oxygen. Similarly, inert gases, such as nitrogen, include a series absorbing bands that may be different than the absorbing bands of oxygen. In some examples, the wavelengths of light beams 98 and 102 can be selected to be within the absorbing bands of the inert gas. Absorption is distance dependent, so the distance that light beams 98 and 102 travel prior to arriving at imagers 90 and 102, respectively, must be known.

The light received at imagers 90 and 102 may be analyzed by controller 28, for example, to determine an amount of absorption of the at least one wavelength corresponding to a selected constituent of ullage gases 96, such as oxygen, inert gas (e.g., nitrogen gas), or other selected constituent. For example, an intensity of light received by imagers 90 and 102 may be known as a reference for when no oxygen is present. This reference may be compared to the active intensity of light received by imagers 90 and 102 to determine an amount of absorption of the at least one wavelength. This amount of absorption along with the known distance of travel for beams 98 and 102, may be utilized to determine a level of a constituent, such as oxygen, inert gas, or other constituent within ullage gases 96. Such determined levels of constituent can be indicative of an operational status of the inert gas generating system. For instance, a presence of oxygen or amount of oxygen that exceeds a threshold acceptability value can indicate a leak or other malfunction of the inert gas generating system configured to generate the oxygen-depleted air.

Controller 28 can determine the operational status of the inert gas generating system based on the determined amount of absorption of the at least one wavelength of one or more of light beams 98 and 102. For instance, controller 28 can determine an amount of a constituent, such as oxygen, nitrogen, or other constituent of ullage gases 96 based on the determined absorption. Controller 28 can determine the operational status of the inert gas generating system corresponding to a failure mode of the inert gas generating system in response to determining that the amount of the constituent present in ullage gases 96 deviates from one or more threshold acceptability criteria.

As one example, the one or more threshold acceptability criteria can include a threshold maximum limit corresponding to a maximum acceptable amount of the constituent (e.g., oxygen). Controller 28 can determine that the amount of constituent present in ullage gases 96 deviates from the one or more threshold acceptability criteria in response to determining that the amount of constituent present in ullage gases 96 exceeds the threshold maximum limit corresponding to the maximum acceptable amount of the constituent. As another example, the one or more threshold acceptability criteria can include a threshold minimum limit corresponding to a minimum acceptable amount of the constituent (e.g., nitrogen gas or other inert gas). Controller 28 can determine that the amount of constituent present in ullage gases 96 deviates from the one or more threshold acceptability criteria in response to determining that the amount of constituent present in ullage gases 96 is less than the threshold minimum limit corresponding to the minimum acceptable amount of the constituent.

Accordingly, controller 28, implementing techniques of this disclosure, can determine an operational status of an inert gas generating system configured to generate oxygen-depleted air for ullage of fuel tank 12. As such, the techniques described herein can increase awareness of the operational status of the inert gas generating system, thereby increasing system safety. While described with reference to imagers 92 and 100, in other embodiments, a single photo sensor may also be utilized in place of imagers 92 and 100 to detect an intensity of light from beams 98 and 102, respectively.

With continued reference to FIGS. 1-8B, FIGS. 9-13 are flow diagrams illustrating example operations for determining properties of a fuel tank utilizing one or more image capture devices. For purposes of clarity and ease of discussion, the example operations are described below within the context of fuel tank monitoring system 10 and the embodiments described above.

Figure 9:
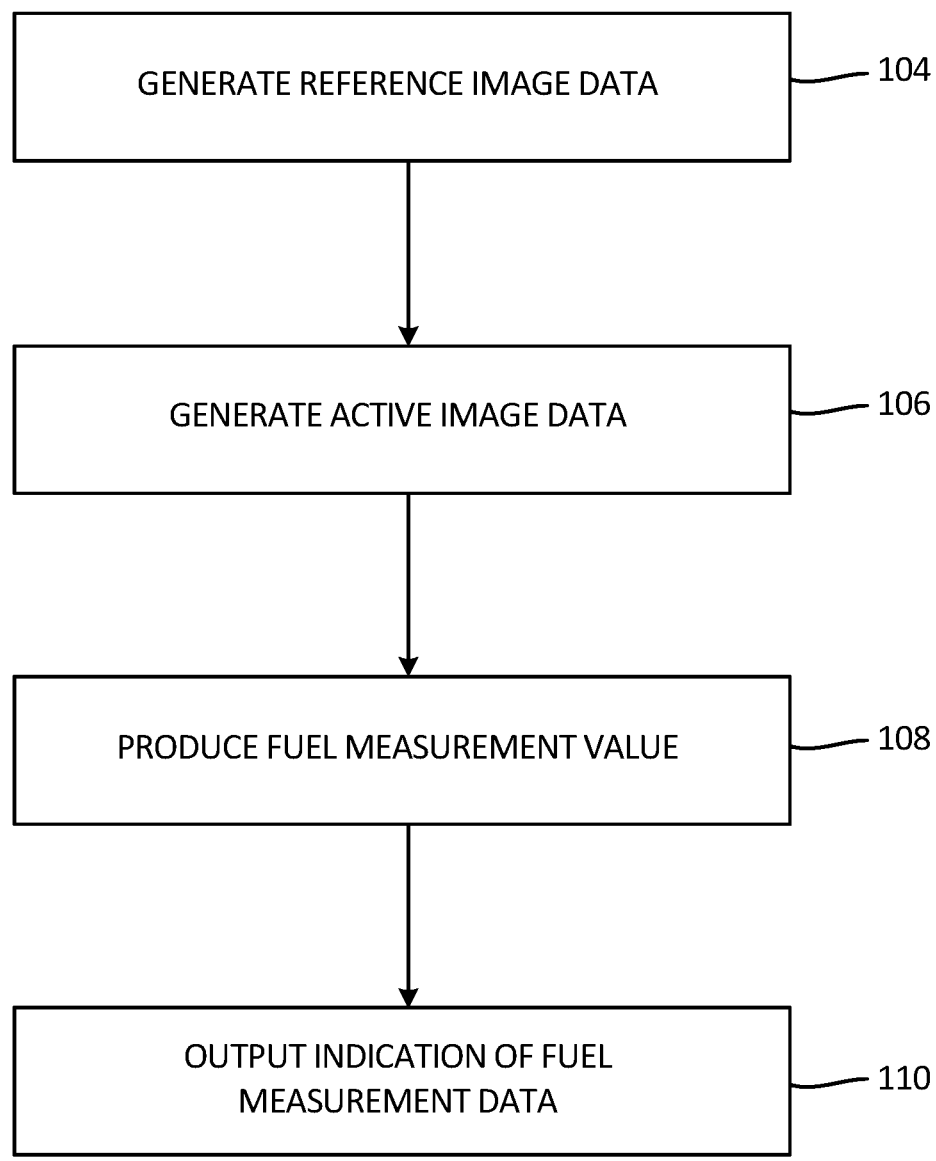
FIGS. 9-13 are flow diagrams illustrating example operations for determining properties of a fuel tank utilizing one or more image capture devices.

FIG. 9 is a flow diagram illustrating example operations to produce a fuel measurement value representing an amount of fuel contained in a fuel tank based on reference image data and active image data of an interior of the fuel tank. Reference image data can be generated representing a field of view of an interior of a fuel tank (Step 104). For example, imager 16a can generate reference image 30a representing a field of view of the interior of fuel tank 12. Active image data can be generated representing the field of view of the interior of the fuel tank when the fuel tank contains fuel (Step 106). For instance, imager 16a can generate active image 30b representing the field of view of the interior of fuel tank 12 when fuel tank 12 contains fuel. A fuel measurement value can be produced representing an amount of fuel contained in the fuel tank based on the reference image data and the active image data (Step 108). As an example, controller 28 can produce a fuel measurement value representing a volume of fuel contained in fuel tank 12 based on image processing techniques to locate fuel level lines 32a-32c and determine the volume of fuel based on a correspondence of fuel level lines 32a-32c with one or more physical features of the interior of fuel tank 12. An indication of the fuel measurement value can be provided as output (Step 110). For instance, controller 28 can output data including the fuel measurement value via one or more communication data buses.

Figure 10:
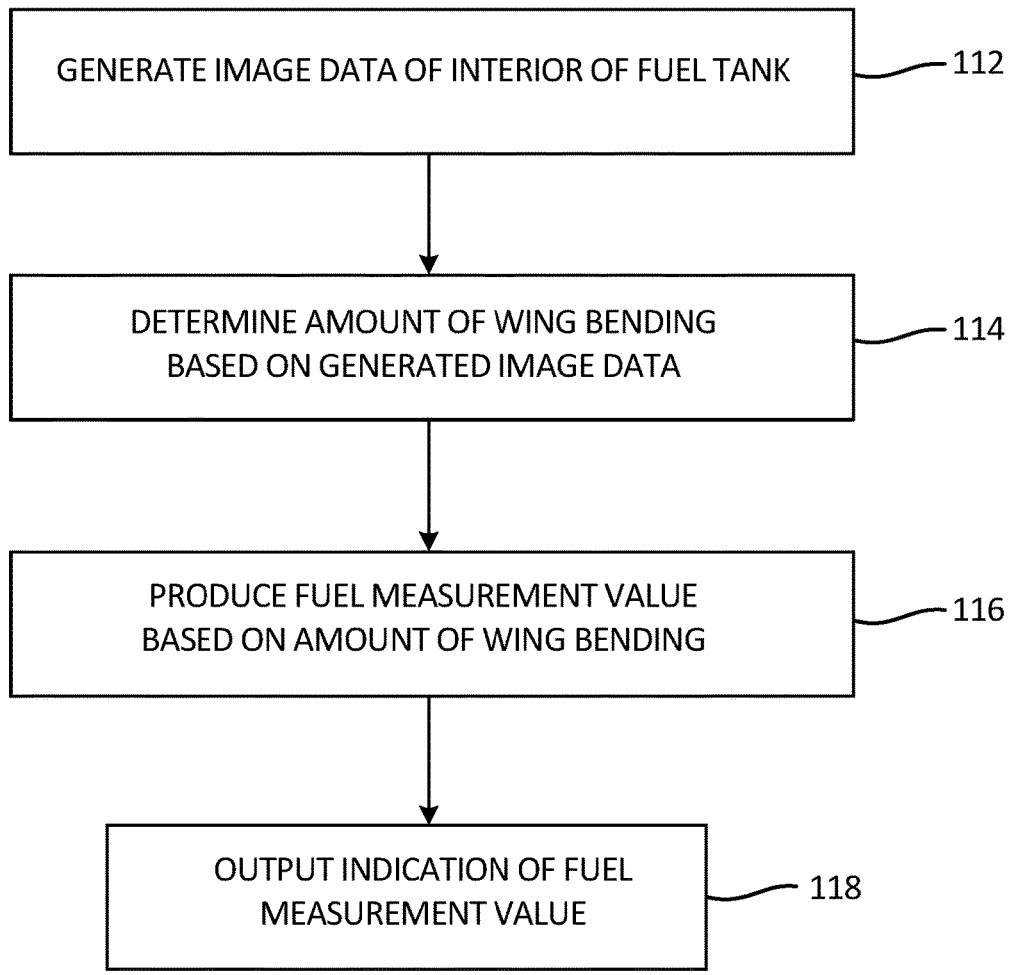

FIG. 10 is a flow diagram illustrating example operations to produce a fuel measurement value representing an amount of fuel contained in a fuel tank disposed within a wing of an aircraft based on a determined amount of wing bending of the wing. Image data can be generated of an interior of a fuel tank disposed within a wing of an aircraft (Step 112). For example, imager 50 can generate reference image data 53a and active image data 53b of the interior of fuel tank 12 disposed within wing 14 of an aircraft. An amount of wing bending of the wing of the aircraft can be determined based on the generated image data of the interior of the fuel tank (Step 114). For instance, controller 28 can determine distances 54a-54c between structural elements 52a-52d for each of reference image data 53a and active image data 53b, and can compare the distances 52a-52d between each of reference image data 53a and active image data 53b to determine angle $\theta_B$ as the determined amount of wing bending of wing 14. A fuel measurement value representing an amount of fuel contained in the fuel tank can be produced based on the amount of wing bending of the wing of the aircraft (Step 116). As an example, controller 28 can modify a shape of fuel tank 12 using a model of the shape of fuel tank 12 based on the determined amount of wing bending, and can determine a fuel measurement value, such as a fuel volume, a fuel mass, or other fuel measurement value based on the modified shape of fuel tank 12 within the model. An indication of the fuel measurement value can be output (Step 118). For instance, controller 28 can output data including the fuel measurement value via one or more communication data buses.

Figure 11:
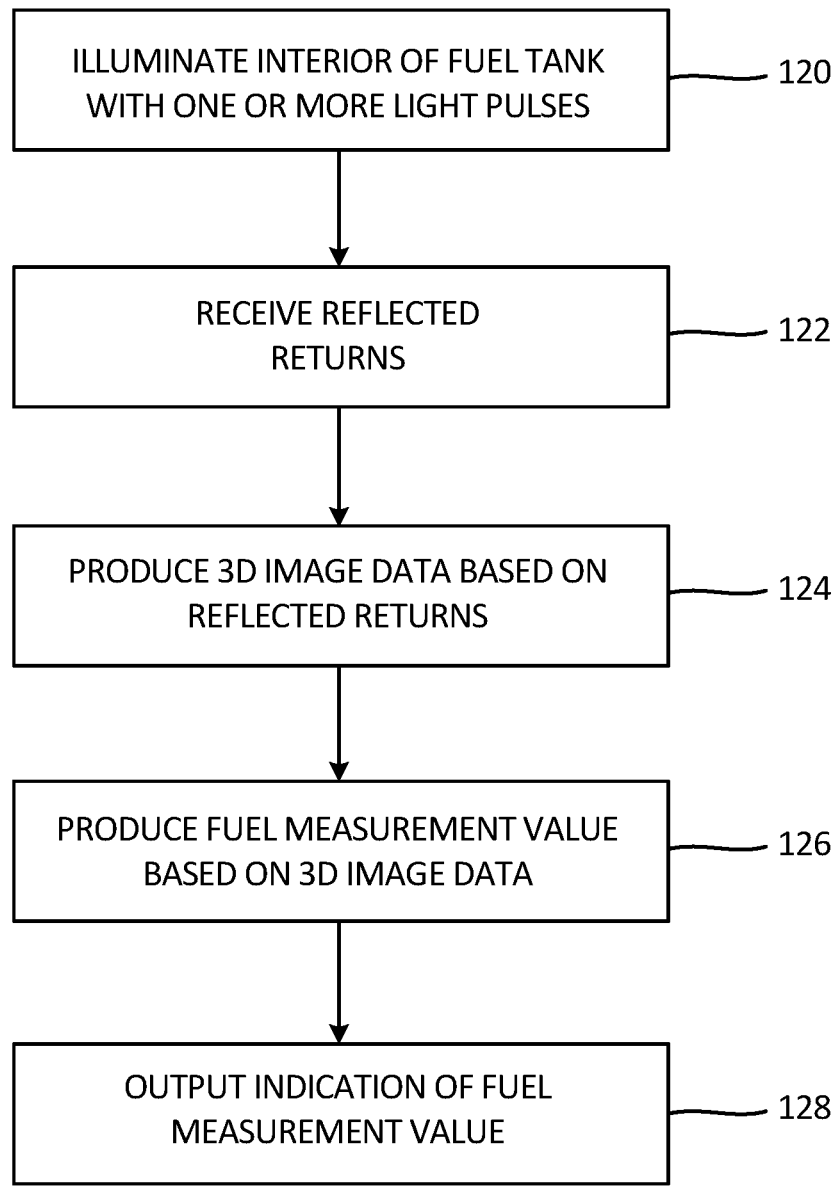

FIG. 11 is a flow diagram illustrating example operations to produce a fuel measurement value representing an amount of fuel contained in a fuel tank based on three-dimensional image data of the interior of the fuel tank. An interior of a fuel tank can be illuminated with one or more light pulses (Step 120). For example, time-of-flight imager 60 can emit light 64 using an integral or separate light source, such as a directional laser light source. Reflected returns of the one or more light pulses can be received at a light sensor array (Step 122). For instance, time-of-flight imager 60 can include a focal plane array that provides an image on a pixel-by-pixel basis. Light 64, after reflection from fuel interface 62 and/or other physical features of the interior of fuel tank 12 (e.g., spars 22, structural features 26, or other physical features) can be received at the focal plane array and analyzed by, e.g., controller 28. Three-dimensional (3D) image data of the interior of the fuel tank can be produced based on the received reflected returns (Step 124). For example, controller 28 can determine the 3D image data by determining a time-of-flight of reflected returns of light 64 for each pixel of the focal plane array. In certain examples, controller 28 can determine the time-of-flight for each pixel based upon an intensity of each pixel (e.g., utilizing range gating techniques). In some examples, controller 28 can determine the time-of-flight directly for each pixel based on an elapsed time between emission of light 64 and receipt of reflected returns of light 64 at each pixel of the focal plane array. In other examples, controller 28 can determine the time-of-flight for each pixel based on a phase change between emitted light 64 and reflected returns of light 64 at each pixel. A fuel measurement value representing an amount of fuel contained in the fuel tank can be produced based on the three-dimensional image data (Step 126). For instance, controller 28 can identify a correspondence (e.g., a location of an intersection) between physical features of the interior of fuel tank 12 and an interface of fuel and ullage within fuel tank 12 based on the three-dimensional image data. Controller 28 can determine a fuel measurement value, such as a volume of fuel contained in fuel tank 12, based on the identified correspondence between the physical features of the interior of fuel tank 12 and the interface of fuel and ullage within fuel tank 12. An indication of the fuel measurement value can be output (Step 128). For instance, controller 28 can output data including the fuel measurement value via one or more communication data buses.

Figure 12:
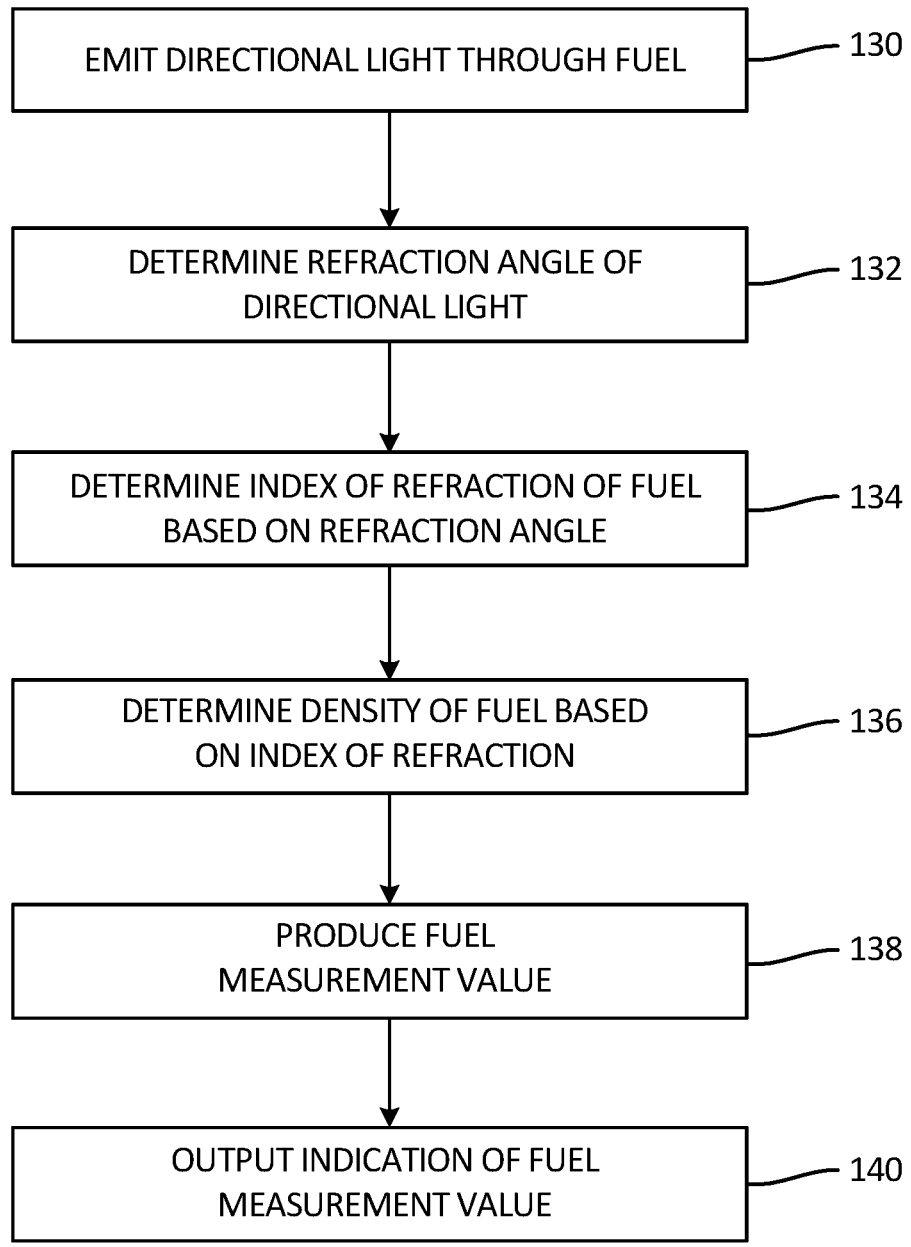

FIG. 12 is a flow diagram illustrating example operations to determine a density of fuel contained in a fuel tank based on a determined index of refraction of the fuel. Directional light can be emitted from a light source through fuel contained in a fuel tank (Step 130). For example, light source 70 can emit directed beam of light 78 through fuel contained in fuel tank 12. A refraction angle of the directional light after the directional light passes through an interface with the fuel can be determined (Step 132). For instance, controller 28 can determine angle $\theta_2$, which can be considered a refraction angle of beam 78 after beam 78 passes through the interface with the fuel (e.g., fuel interface 74 separating ullage gases and fuel within fuel tank 12). An index of refraction of the fuel can be determined based on the determined refraction angle (Step 134). As an example, using both $\theta_1$ and $\theta_2$, controller 28 can utilize Snell's law to determine the index of refraction of the fuel. A density of the fuel can be determined based on the determined index of refraction of the fuel (Step 136). For instance, controller 28 can determine the index of refraction based on angle $\theta_2$ as well as known properties of the fuel and a sensed temperature of the fuel (e.g., sensed via a thermal imager and/or temperature probe disposed within fuel tank 12). A fuel measurement value representing an amount of fuel contained in the fuel tank can be produced based on the determined density of the fuel (Step 138). For example, controller 28 can determine a fuel measurement value representing a mass of fuel contained in fuel tank 12 based on the determined density and a determined volume of the fuel contained in fuel tank 12. An indication of the fuel measurement value can be output. For instance, controller 28 can output data including the fuel measurement value via one or more communication data buses.

Figure 13:
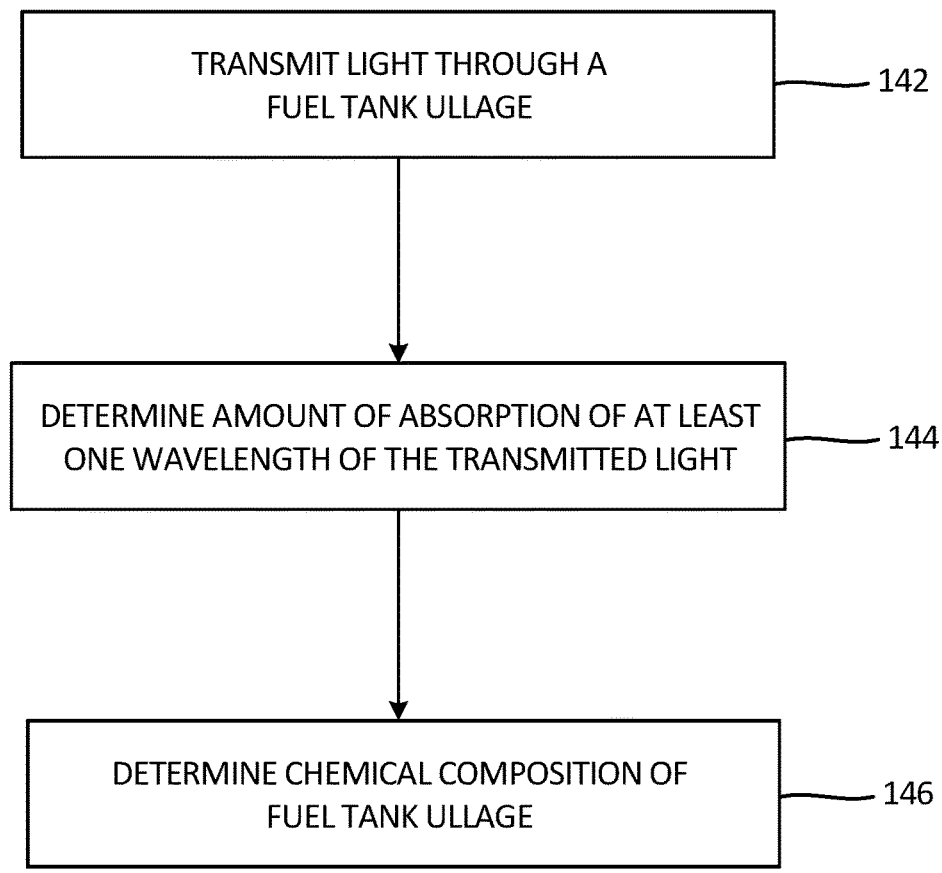

FIG. 13 is a flow diagram illustrating example operations to determine a chemical composition of a fuel tank ullage based on an amount of absorption of at least one wavelength of light transmitted through the fuel tank ullage. Light can be transmitted through a fuel tank ullage (Step 142). For example, light source 90 can emit light through a distance of ullage gases 96 of fuel tank 12. An amount of absorption of at least one wavelength of the transmitted light can be determined (Step 144). For instance, controller 28 can determine, based on an intensity of light received by imagers 90 and/or 102, an absorption of at least one wavelength of the transmitted light. A chemical composition of the fuel tank ullage can be determined (Step 146). As an example, controller 28 can determine a presence and/or amount of a constituent of ullage gases 96 (e.g., oxygen gas, nitrogen gas, or other constituent) based on the amount of absorption of the at least one wavelength of the transmitted light. Controller 28 can, in certain examples, determine an operational status of an inert gas generating system configured to generate oxygen-depleted air for the fuel tank ullage based on the determined amount of absorption of the at least one wavelength of the transmitted light, such as an operational status corresponding to a failure mode of the inert gas generating system based on the presence and/or amount of a constituent of ullage gases 96. For instance, controller 28 can determine the failure mode of the inert gas generating system in response to determining that the amount of the constituent present in the ullage gases 96 deviates from one or more threshold acceptability criteria, such as a maximum limit corresponding to a maximum acceptable amount of the constituent (e.g., a maximum amount of oxygen gas), a minimum limit corresponding to a minimum acceptable amount of the constituent (e.g., a minimum amount of an inert gas, such as nitrogen gas), or other threshold acceptability criteria. Controller 28 can output, in some examples, the operational status of the inert gas generating system (e.g., an operational status corresponding to a failure mode and/or to a non-failure mode) to, e.g., one or more consuming systems, such as a data concentrator unit, an air conditioning system, cockpit displays, or other consuming system(s). Accordingly, controller 28 can help to increase system safety by determining and, e.g., outputting the operational status of the inert gas generating system. In some examples, the determined chemical composition can be used to activate and/or deactivate the inert gas generating system. For instance, when controller 28 determines that an amount of a constituent, such as an inert gas constituent (e.g., nitrogen), satisfies threshold criteria, the inert gas generating system can be turned off or otherwise cease to provide inert gas for the fuel tank ullage. As such, techniques of this disclosure can help to decrease an amount of power (e.g., electrical power) consumed by an inert gas generating system, thereby increasing system efficiency.

As described herein, a fuel tank monitoring system 10 can utilize image processing techniques to determine properties of fuel tank 12, such as physical features of an interior of fuel tank 12 (e.g., locations and/or physical contours of spars 22, ribs 24, structural elements 26, or other physical features of the interior of fuel tank 12), a level and/or volume of fuel within the interior of fuel tank 12, tilt of an aircraft that includes fuel tank 12, an amount of bend of wing 14 of the aircraft, a density of the fuel within fuel tank 12, a chemical composition of fluids within fuel tank 12 (e.g., fuel, gases within an ullage of fuel tank 12, or other fluids within fuel tank 12), and/or a temperature of fluid(s) within fuel tank 12. The techniques can enable such properties to be determined without the use of in-tank capacitive probes, thereby helping to decrease a number of electrical components installed within an interior of fuel tank 12. Moreover, techniques described herein can decrease a total number of installed components, thereby helping to reduce installation and maintenance costs associated with operation of fuel tank monitoring system 10.

Discussion of Possible Embodiments

The following are non-exclusive descriptions of possible embodiments of the present invention.

A method can include generating reference image data representing a field of view of an interior of a fuel tank and generating active image data representing the field of view of the interior of the fuel tank when the fuel tank contains fuel. The method can further include producing, by a processing device, a fuel measurement value representing an amount of fuel contained in the fuel tank based on the reference image data and the active image data, and outputting, by the processing device, an indication of the fuel measurement value.

The method of the preceding paragraph can optionally include, additionally and/or alternatively, any one or more of the following features, configurations, operations, and/or additional components:

Generating the reference image data can include generating the reference image data when the fuel tank is empty of fuel.

Producing the fuel measurement value can include: identifying, based on the reference image data, physical features of the interior of the fuel tank; identifying, based on the active image data, a location of the interior of the fuel tank corresponding to an interface of fuel and ullage within the interior of the fuel tank; identifying a location of the interior of the fuel tank corresponding to an intersection of the interface of fuel and ullage with one or more of the physical features of the interior of the fuel tank; and producing the fuel measurement value based on the location of the interior of the fuel tank corresponding to the intersection of the interface of fuel and ullage with the one or more of the physical features of the interior of the fuel tank.

Producing the fuel measurement value based on the location of the interior of the fuel tank corresponding to the intersection of the interface of fuel and ullage with the one or more of the physical features of the interior of the fuel tank can include determining, based on a model of a shape of the fuel tank, a volume of fuel contained within the fuel tank.

The method can further include determining an adjusted shape of the fuel tank based on the active image data using a model of the shape of the fuel tank. Producing the fuel measurement value can include determining the volume of fuel within the fuel tank based on the adjusted shape of the fuel tank.

The fuel tank can be disposed within a wing of the aircraft. Determining the adjusted shape of the fuel tank can include determining an amount of wing bending of the wing of the aircraft.

Determining the amount of wing bending of the wing of the aircraft can include: determining a displacement of the one or more of the physical features between the reference image data and the active image data; and determining the amount of wing bending based on the determined displacement of the one or more of the physical features.

Generating the active image data representing the field of view of the interior of the fuel tank can include generating first active image data representing a first field of view of the interior of the fuel tank. The method can further include generating second active image data representing a second field of view of the interior of the fuel tank when the fuel tank contains fuel. Producing the fuel measurement value can include producing the fuel measurement value representing the amount of fuel contained in the fuel tank based on the reference image data and the first and second active image data.

The first field of view of the interior of the fuel tank can include an upper portion of the interior of the fuel tank. The second field of view of the interior of the fuel tank can include a lower portion of the interior of the fuel tank. Generating the first active image data can include generating the first active image data using an image capturing device disposed at the lower portion of the interior of the fuel tank. Generating the second active image data can include generating the second active image data using an image capturing device disposed at the upper portion of the interior of the fuel tank.

Generating the first active image data representing the first field of view including the upper portion of the interior of the fuel tank can include illuminating the interior of the fuel tank using a light source disposed at the upper portion of the interior of the fuel tank.

Generating the first active image data representing the first field of view including the upper portion of the interior of the fuel tank can include illuminating the interior of the fuel tank using a light source disposed at the lower portion of the interior of the fuel tank.

Generating the second active image data representing the second field of view including the lower portion of the interior of the fuel tank can include illuminating the interior of the fuel tank using a light source disposed at the lower portion of the interior of the fuel tank.

Generating the second active image data representing the second field of view including the lower portion of the interior of the fuel tank can include illuminating the interior of the fuel tank using a light source disposed at the upper portion of the interior of the fuel tank.

Generating the active image data can include generating the active image data using one or more image capturing devices disposed within an interior of the fuel tank.

Generating the active image data can include generating the active image data using one or more image capturing devices disposed external to the interior of the fuel tank.

A system can include one or more image capturing devices, at least one process, and computer-readable memory. The one or more image capturing devices can be located to: generate reference image data representing of an interior of a fuel tank; and generate active image data of the interior of the fuel tank when the fuel tank contains fuel. The computer-readable memory can be encoded with instructions that, when executed by the at least one processor, cause the system to: produce a fuel measurement value representing an amount of fuel contained in the fuel tank based on the reference image data and the active image data; and output an indication of the fuel measurement value.

The system of the preceding paragraph can optionally include, additionally and/or alternatively, any one or more of the following features, configurations, operations, and/or additional components:

The computer-readable memory can be further encoded with instructions that, when executed by the at least one processor, cause the system to produce the fuel measurement value by at least causing the system to: identify, based on the reference image data, physical features of the interior of the fuel tank; identify, based on the active image data, a location of the interior of the fuel tank corresponding to an interface of fuel and ullage within the interior of the fuel tank; identify a location of the interior of the fuel tank corresponding to an intersection of the interface of fuel and ullage with one or more of the physical features of the interior of the fuel tank; and produce the fuel measurement value based on the location of the interior of the fuel tank corresponding to the intersection of the interface of fuel and ullage with the one or more of the physical features of the interior of the fuel tank.

The computer-readable memory can be further encoded with instructions that, when executed by the at least one processor, cause the system to produce the fuel measurement value based on the location of the interior of the fuel tank corresponding to the intersection of the interface of fuel and ullage with the one or more of the physical features of the interior of the fuel tank by at least causing the system to determine, based on a model of a shape of the fuel tank, a volume of fuel contained within the fuel tank.

The fuel tank can be disposed within a wing of an aircraft. The computer-readable memory can be further encoded with instructions that, when executed by the at least one processor, cause the system to: determine an amount of wing bending of the wing of the aircraft; determine an adjusted shape of the fuel tank based on the determined amount of wing bending using a model of the shape of the fuel tank; and produce the fuel measurement value by at least determining the volume of fuel within the fuel tank based on the adjusted shape of the fuel tank.

The active image data of the interior of the fuel tank can include first active image data representing a first field of view of the interior of the fuel tank. The one or more image capturing devices can be further located to generate second active image data of the interior of the fuel tank when the fuel tank contains fuel. The computer-readable memory can be further encoded with instructions that, when executed by the at least one processor, cause the system to produce the fuel measurement value by at least causing the system to produce the fuel measurement value based on the reference image data and the first and second active image data.

The one or more image capturing devices can include: a first image capturing device located at a lower portion of the interior of the fuel tank to generate the first active image data representing the first field of view of the interior of the fuel tank, wherein the first field of view includes an upper portion of the interior of the fuel tank; and a second image capturing device located at the upper portion of the interior of the fuel tank to generate the second active image data representing the second field of view of the interior of the fuel tank, wherein the second field of view includes the lower portion of the interior of the fuel tank.

A method can include generating image data of an interior of a fuel tank disposed within a wing of an aircraft, and determining, by a processing device, an amount of wing bending of the wing of the aircraft based on the generated image data of the interior of the fuel tank. The method can further include producing, by the processing device, a fuel measurement value representing an amount of fuel contained in the fuel tank based on the amount of wing bending of the wing of the aircraft, and outputting, by the processing device, an indication of the fuel measurement value.

The method of the preceding paragraph can optionally include, additionally and/or alternatively, any one or more of the following features, configurations, operations, and/or additional components:

Generating the image data of the interior of the fuel tank can include generating active image data when the fuel tank contains fuel. The method can further include generating reference image data of the interior of the fuel tank. Determining the amount of wing bending of the wing of the aircraft can include determining the amount of wing bending of the wing of the aircraft based on the active image data and the reference image data.

Determining the amount of wing bending can include: determining, based on the active image data and the reference image data, a displacement of one or more physical features of the interior of the fuel tank; and determining the amount of wing bending based on the determined displacement of the one or more physical features.

Producing the fuel measurement value can include: adjusting a shape of the fuel tank based on the determined amount of wing bending using a model of the shape of the fuel tank; and producing the fuel measurement value based on the adjusted shape of the fuel tank.

Producing the fuel measurement value representing the amount of fuel contained in the fuel tank based on the adjusted shape of the fuel tank can include: identifying, based on the generated image data, a location of the interior of the fuel tank corresponding to an interface of fuel and ullage within the interior of the fuel tank; identifying a location of an intersection of the interface of fuel and ullage with one or more physical features identified in the model of the adjusted shape of the fuel tank; and determining a volume of fuel contained within the fuel tank based on the identified location of the intersection of the interface of fuel and ullage with the one or more physical features identified in the model of the adjusted shape of the fuel tank.

Generating the image data of the interior of the fuel tank can include generating the image data using one or more image capturing devices located to generate the image data of the interior of the fuel tank.

The one or more image capturing devices can include a plurality of image capturing devices disposed at a plurality of locations to include a plurality of fields of view of the interior of the fuel tank.

A device can include at least one processor and computer-readable memory. The computer-readable memory can be encoded with instructions that, when executed by the at least one processor, cause the device to: receive image data of an interior of a fuel tank disposed within a wing of an aircraft; determine an amount of wing bending of the wing of the aircraft based on the received image data of the interior of the fuel tank; produce a fuel measurement value representing an amount of fuel contained in the fuel tank based on the amount of wing bending of the wing of the aircraft; and output the fuel measurement value.

The device of the preceding paragraph can optionally include, additionally and/or alternatively, any one or more of the following features, configurations, operations, and/or additional components:

The received image data of the interior of the fuel tank disposed within the wing of the aircraft can include active image data generated when the fuel tank contains fuel. The computer-readable memory can be further encoded with instructions that, when executed by the at least one processor, cause the device to: receive reference image data of the interior of the fuel tank; and determine the amount of wing bending of the wing of the aircraft by at least determining the amount of wing bending of the wing of the aircraft based on the active image data and the reference image data.

The computer-readable memory can be further encoded with instructions that, when executed by the at least one processor, cause the device to determine the amount of wing bending by at least causing the device to: determine, based on the active image data and the reference image data, a displacement of one or more physical features of the interior of the fuel tank; and determine the amount of wing bending based on the determined displacement of the one or more physical features.

The computer-readable memory can be further encoded with instructions that, when executed by the at least one processor, cause the device to produce the fuel measurement value by at least causing the device to: adjust a shape of the fuel tank based on the determined amount of wing bending using a model of the shape of the fuel tank; and produce the fuel measurement value based on the adjusted shape of the fuel tank.

The computer-readable memory can be further encoded with instructions that, when executed by the at least one processor, cause the device to produce the fuel measurement value representing the amount of fuel contained in the fuel tank based on the adjusted shape of the fuel tank by at least causing the device to: identify, based on the generated image data, a location of the interior of the fuel tank corresponding to an interface of fuel and ullage within the interior of the fuel tank; identify a location of an intersection of the interface of fuel and ullage with one or more physical features identified in the model of the adjusted shape of the fuel tank; and determine a volume of fuel contained within the fuel tank based on the identified location of the intersection of the interface of fuel and ullage with the one or more physical features identified in the model of the adjusted shape of the fuel tank.

The computer-readable memory can be further encoded with instructions that, when executed by the at least one processor, cause the device to receive the image data of the interior of the fuel tank by at least causing the device to receive the image data from one or more image capturing devices located to generate the image data of the interior of the fuel tank.

A system can include one or more image capturing devices, at least one processor, and computer-readable memory. The one or more image capturing devices can be located to generate image data of an interior of a fuel tank disposed within a wing of an aircraft. The computer-readable memory can be encoded with instructions that, when executed by the at least one processor, cause the system to: generate, using the one or more image capturing devices, the image data of the interior of the fuel tank disposed within the wing of the aircraft; determine and amount of wing bending of the wing of the aircraft based on the generated image data of the interior of the fuel tank; produce a fuel measurement value representing an amount of fuel contained in the fuel tank based on the amount of wing bending of the wing of the aircraft; and output the fuel measurement value.

The system of the preceding paragraph can optionally include, additionally and/or alternatively, any one or more of the following features, configurations, operations, and/or additional components:

The generated image data of the interior of the fuel tank disposed within the wing of the aircraft can include active image data generated when the fuel tank contains fuel. The computer-readable memory can be further encoded with instructions that, when executed by the at least one processor, cause the system to: generate, using the one or more image capturing devices, reference image data of the interior of the fuel tank; and determine the amount of wing bending of the wing of the aircraft by at least determining the amount of wing bending of the wing of the aircraft based on the active image data and the reference image data.

The computer-readable memory can be further encoded with instructions that, when executed by the at least one processor, cause the system to determine the amount of wing bending by at least causing the system to: determine, based on the active image data and the reference image data, a displacement of one or more physical features of the interior of the fuel tank; and determine the amount of wing bending based on the determined displacement of the one or more physical features.

The computer-readable memory can be further encoded with instructions that, when executed by the at least one processor, cause the system to produce the fuel measurement value by at least causing the system to: adjust a shape of the fuel tank based on the determined amount of wing bending using a model of the shape of the fuel tank; and produce the fuel measurement value representing the amount of fuel contained in the fuel tank based on the adjusted shape of the fuel tank.

The computer-readable memory can be further encoded with instructions that, when executed by the at least one processor, cause the system to produce the fuel measurement value representing the amount of fuel contained in the fuel tank based on the adjusted shape of the fuel tank by at least causing the system to: identify, based on the generated image data, a location of the interior of the fuel tank corresponding to an interface of fuel and ullage within the interior of the fuel tank; identify a location of an intersection of the interface of fuel and ullage with one or more physical features identified in the model of the adjusted shape of the fuel tank; and determine a volume of fuel contained within the fuel tank based on the identified location of the intersection of the interface of fuel and ullage with the one or more physical features identified in the model of the adjusted shape of the fuel tank.

The one or more image capturing devices can include a plurality of image capturing devices disposed at a plurality of locations to include a plurality of fields of view of the interior of the fuel tank.

An aggregate of the plurality of fields of view of the interior of the fuel tank comprise an entirety of the interior of the fuel tank.

A method can include illuminating an interior of a fuel tank with one or more light pulses, receiving reflected returns of the one or more light pulses at a light sensor array, and producing, by a processing device, three-dimensional image data of the interior of the fuel tank based on the received reflected returns. The method can further include producing, by the processing device, a fuel measurement value representing an amount of fuel contained in the fuel tank based on the three-dimensional image data, and outputting, by the processing device, an indication of the fuel measurement value.

The method of the preceding paragraph can optionally include, additionally and/or alternatively, any one or more of the following features, configurations, operations, and/or additional components:

Producing the three-dimensional image data of the interior of the fuel tank based on the received reflected returns can include associating each pixel of a plurality of pixels of the three-dimensional image data with an intensity and a distance traveled of a received reflected return associated with the pixel.

Associating each pixel of the plurality of pixels of the three-dimensional image data with the distance traveled of the received reflected return associated with the pixel can include determining the distance traveled of the received reflected return based on a time-of-flight of the received reflected return.

Associating each pixel of the plurality of pixels of the three-dimensional image data with the distance traveled of the received reflected return associated with the pixel can include determining the distance traveled of the received reflected return based on a phase-shift of the received reflected return.

Producing the fuel measurement value representing the amount of fuel contained in the fuel tank based on the three-dimensional image data can include: identifying, based on the three-dimensional image data, physical features of the interior of the fuel tank; identifying, based on the three-dimensional image data, a location of the interior of the fuel tank corresponding to an interface of fuel and ullage within the interior of the fuel tank; and producing the fuel measurement value based on the location of the interior of the fuel tank corresponding to the interface of fuel and ullage within the interior of the fuel tank.

Producing the fuel measurement value based on the location of the interior of the fuel tank corresponding to the interface of fuel and ullage within the interior of the fuel tank can include identifying a location of the interior of the fuel tank corresponding to an intersection of the interface of fuel and ullage with one or more of the physical features of the interior of the fuel tank.

Producing the fuel measurement value based on the location of the interior of the fuel tank corresponding to the interface of fuel and ullage within the interior of the fuel tank can include determining, based on a model of a shape of the fuel tank, a volume of fuel contained within the fuel tank.

The fuel tank can be disposed within a wing of an aircraft. The method can further include: determining an amount of wing bending of the wing of the aircraft; and determining an adjusted shape of the fuel tank based on the determined amount of wing bending using a model of the shape of the fuel tank. Producing the fuel measurement value can include determining the volume of fuel within the fuel tank based on the adjusted shape of the fuel tank.

Determining the amount of wing bending of the wing of the aircraft can include determining a displacement of the one or more of the physical features between a reference location of the one or more of the physical features and a location of the one or more physical features within the three-dimensional image data.

The method can further include determining the reference location of the one or more of the physical features based on the model of the shape of the fuel tank.

A system can include a light source, a light sensor array, at least one processor, and computer-readable memory. The computer-readable memory can be encoded with instructions that, when executed by the at least one processor, cause the system to: illuminate an interior of a fuel tank with one or more light pulses emitted from the light source; produce three-dimensional image data of the interior of the fuel tank based on reflected returns of the one or more light pulses received at the light sensor array; produce a fuel measurement value representing an amount of fuel contained in the fuel tank based on the three-dimensional image data; and output an indication of the fuel measurement value.

The system of the preceding paragraph can optionally include, additionally and/or alternatively, any one or more of the following features, configurations, operations, and/or additional components:

The computer-readable memory can be further encoded with instructions that, when executed by the at least one processor, cause the system to produce the three-dimensional image data of the interior of the fuel tank by at least causing the system to associate each pixel of a plurality of pixels of the three-dimensional image data with an intensity and a distance traveled of a received reflected return associated with the pixel.

The computer-readable memory can be further encoded with instructions that, when executed by the at least one processor, cause the system to associate each pixel of the plurality of pixels of the three-dimensional image data with the distance traveled of the received reflected return associated with the pixel by at least causing the system to determine the distance traveled of the received reflected return based on a time-of-flight of the received reflected return.

The computer-readable memory can be further encoded with instructions that, when executed by the at least one processor, cause the system to associate each pixel of the plurality of pixels of the three-dimensional image data with the distance traveled of the received reflected return associated with the pixel by at least causing the system to determine the distance traveled of the received reflected return based on a phase-shift of the received reflected return.

The computer-readable memory can be further encoded with instructions that, when executed by the at least one processor, cause the system to produce the fuel measurement value representing the amount of fuel contained in the fuel tank based on the three-dimensional image data by at least causing the system to: identify, based on the three-dimensional image data, physical features of the interior of the fuel tank; identify, based on the three-dimensional image data, a location of the interior of the fuel tank corresponding to an interface of fuel and ullage within the interior of the fuel tank; and produce the fuel measurement value based on the location of the interior of the fuel tank corresponding to the interface of fuel and ullage within the interior of the fuel tank.

The computer-readable memory can be further encoded with instructions that, when executed by the at least one processor, cause the system to produce the fuel measurement value based on the location of the interior of the fuel tank corresponding to the interface of fuel and ullage within the interior of the fuel tank by at least causing the system to identify a location of the interior of the fuel tank corresponding to an intersection of the interface of fuel and ullage with one or more of the physical features of the interior of the fuel tank.

The computer-readable memory can be further encoded with instructions that, when executed by the at least one processor, cause the system to produce the fuel measurement value based on the location of the interior of the fuel tank corresponding to the interface of fuel and ullage within the interior of the fuel tank by at least causing the system to determine, based on a model of a shape of the fuel tank, a volume of fuel contained within the fuel tank.

The fuel tank can be disposed within a wing of an aircraft. The computer-readable memory can be further encoded with instructions that, when executed by the at least one processor, cause the system to: determine an amount of wing bending of the wing of the aircraft; determine an adjusted shape of the fuel tank based on the determined amount of wing bending using a model of the shape of the fuel tank; and produce the fuel measurement value by determining the volume of fuel within the fuel tank based on the adjusted shape of the fuel tank.

The computer-readable memory can be further encoded with instructions that, when executed by the at least one processor, cause the system to determine the amount of wing bending of the wing of the aircraft by at least causing the system to determine a displacement of the one or more of the physical features between a reference location of the one or more of the physical features and a location of the one or more physical features within the three-dimensional image data.

The computer-readable memory can be further encoded with instructions that, when executed by the at least one processor, cause the system to determine the reference location of the one or more of the physical features based on the model of the shape of the fuel tank.

A device can include at least one processor and computer-readable memory. The computer-readable memory can be encoded with instructions that, when executed by the at least one processor, cause the device to: produce three-dimensional image data of an interior of a fuel tank based on received reflected returns of one or more light pulses used to illuminate the interior of the fuel tank; produce a fuel measurement value representing an amount of fuel contained in the fuel tank based on the three-dimensional image data; and output an indication of the fuel measurement value.

The device of the preceding paragraph can optionally include, additionally and/or alternatively, any one or more of the following features, configurations, operations, and/or additional components:

The computer-readable memory can be further encoded with instructions that, when executed by the at least one processor, cause the device to produce the fuel measurement value representing the amount of fuel contained in the fuel tank based on the three-dimensional image data by at least causing the system to: identify, based on the three-dimensional image data, physical features of the interior of the fuel tank; identify, based on the three-dimensional image data, a location of the interior of the fuel tank corresponding to an interface of fuel and ullage within the interior of the fuel tank; and produce the fuel measurement value based on the location of the interior of the fuel tank corresponding to the interface of fuel and ullage within the interior of the fuel tank.

A method can include emitting, from a light source, directional light through fuel contained in a fuel tank, determining a refraction angle of the directional light after the directional light passes through an interface with the fuel, and determining, by a processing device, an index of refraction of the fuel based on the determined refraction angle. The method can further include determining, by the processing device, a density of the fuel based on the determined index of refraction of the fuel.

The method of the preceding paragraph can optionally include, additionally and/or alternatively, any one or more of the following features, configurations, operations, and/or additional components:

The method can further include producing, by the processing device, a fuel measurement value representing an amount of fuel contained in the fuel tank based on the determined density of the fuel, and outputting, by the processing device, an indication of the fuel measurement value.

Producing the fuel measurement value representing the amount of fuel contained in the fuel tank based on the determined density of the fuel can include determining a mass of the fuel contained in the fuel tank based on a determined volume of the fuel contained in the fuel tank and the determined density of the fuel.

Determining the refraction angle of the directional light can include identifying, using an image capturing device, a location of an interior of the fuel tank intersected by the directional light after the directional light passes through the interface with the fuel.

Determining the refraction angle of the directional light can further include determining a distance between the location of the interior of the fuel tank intersected by the directional light and a location of the interior of the fuel tank corresponding to non-refraction of the directional light.

The method can further include measuring, using a thermal imaging device, a temperature of the fuel. Determining the density of the fuel based on the determined index of refraction of the fuel can include determining the density of the fuel based on the determined index of refraction of the fuel and the measured temperature of the fuel.

The light source can include a laser light source.

The interface with the fuel can include an interface between the fuel and ullage gas of the fuel tank.

A system can include a light source, at least one processor, and computer-readable memory. The light source can be configured to emit directional light. The computer-readable memory can be encoded with instructions that, when executed by the at least one processor, cause the system to: emit the directional light from the light source through fuel contained in a fuel tank; determine a refraction angle of the directional light after the directional light passes through an interface with the fuel; determine an index of refraction of the fuel based on the measured refraction angle; and determine a density of the fuel based on the determined index of refraction of the fuel.

The system of the preceding paragraph can optionally include, additionally and/or alternatively, any one or more of the following features, configurations, operations, and/or additional components:

The computer-readable memory can be further encoded with instructions that, when executed by the at least one processor, cause the system to: produce a fuel measurement value representing an amount of fuel contained in the fuel tank based on the determined density of the fuel; and output an indication of the fuel measurement value.

The computer-readable memory can be further encoded with instructions that, when executed by the at least one processor, cause the system to produce the fuel measurement value representing the amount of fuel contained in the fuel tank based on the determined density of the fuel by at least causing the system to determine a mass of the fuel contained in the fuel tank based on a determined volume of the fuel contained in the fuel tank and the determined density of the fuel.

The system can further include an image capturing device located to include a field of view of an interior of the fuel tank. The computer-readable memory can be further encoded with instructions that, when executed by the at least one processor, cause the system to determine the refraction angle of the directional light by at least causing the system to: generate image data of the interior of the fuel tank using the image capturing device; and identify, using the image data, a location of the interior of the fuel tank intersected by the directional light after the directional light passes through the interface with the fuel.

The computer-readable memory can be further encoded with instructions that, when executed by the at least one processor, cause the system to determine the refraction angle of the directional light by at least causing the system to determine, using the image data, a distance between the location of the interior of the fuel tank intersected by the directional light and a location of the interior of the fuel tank corresponding to non-refraction of the directional light.

The system can further include a thermal imaging device located to include a field of view of an interior of the fuel tank. The computer-readable memory can be further encoded with instructions that, when executed by the at least one processor, cause the system to determine the density of the fuel based on the determined index of refraction of the fuel by at least causing the system to determine the density of the fuel based on the determined index of refraction of the fuel and a temperature of the fuel measured using the thermal imaging device.

The light source can include a laser light source.

The interface with the fuel can include an interface between the fuel and ullage gas of the fuel tank.

A device can include at least one processor and computer-readable memory. The computer-readable memory can be encoded with instructions that, when executed by the at least one processor, cause the device to: determine a refraction angle of directional light emitted from a light source through fuel contained in a fuel tank after the directional light passes through an interface with the fuel; determine an index of refraction of the fuel based on the measured refraction angle; and determine a density of the fuel based on the determined index of refraction of the fuel.

The device of the preceding paragraph can optionally include, additionally and/or alternatively, any one or more of the following features, configurations, operations, and/or additional components:

The computer-readable memory can be further encoded with instructions that, when executed by the at least one processor, cause the device to: produce a fuel measurement value representing an amount of fuel contained in the fuel tank based on the determined density of the fuel; and output an indication of the fuel measurement value The computer-readable memory can be further encoded with instructions that, when executed by the at least one processor, cause the device to determine the refraction angle of the directional light by at least causing the device to identify, using the image data generated by an image capturing device located to include a field of view of the interior of the fuel tank, a location of the interior of the fuel tank intersected by the directional light after the directional light passes through the interface with the fuel.

The computer-readable memory can be further encoded with instructions that, when executed by the at least one processor, cause the device to determine the refraction angle of the directional light by at least causing the device to determine, using the image data, a distance between the location of the interior of the fuel tank intersected by the directional light and a location of the interior of the fuel tank corresponding to non-refraction of the directional light.

The computer-readable memory can be further encoded with instructions that, when executed by the at least one processor, cause the device to determine the density of the fuel based on the determined index of refraction of the fuel by at least causing the device to determine the density of the fuel based on the determined index of refraction of the fuel and a temperature of the fuel measured using a thermal imaging device.

The light source can include a laser light source. The interface with the fuel can include an interface between the fuel and ullage gas of the fuel tank.

A method can include transmitting, from a light source, light through a fuel tank ullage, and determining, by a processing device, an amount of absorption of at least one wavelength of the transmitted light. The method can further include determining, by the processing device based on the amount of absorption of the at least one wavelength of the transmitted light, a chemical composition of the fuel tank ullage.

The method of the preceding paragraph can optionally include, additionally and/or alternatively, any one or more of the following features, configurations, operations, and/or additional components:

Determining the amount of absorption of the at least one wavelength of the transmitted light can include: receiving the transmitted light at an image sensing device after the light is transmitted through the fuel tank ullage; measuring an intensity of the at least one wavelength received at the image sensing device; measuring an intensity of the at least one wavelength transmitted by the light source; and determining the amount of absorption of the at least one wavelength based on a change between the measured intensity of the at least one wavelength transmitted by the light source and the measured intensity of the at least one wavelength received at the image sensing device.

The image sensing device can be disposed at a location that is remote from the light source.

The image sensing device can be co-located with the light source. Receiving the transmitted light at the image sensing device after the light is transmitted through the fuel tank ullage can include receiving a reflection of the transmitted light after the transmitted light is reflected from a location that is a distance from the light source.

Determining the chemical composition of the fuel tank ullage can include determining presence of a constituent in the fuel tank ullage based on the determined amount of absorption of the at least one wavelength. The method can further include determining, based on the determined presence of the constituent in the fuel tank ullage, an operational status of an inert gas generating system configured to produce oxygen-depleted air for the fuel tank ullage.

The at least one wavelength of the transmitted light can include an absorption wavelength of oxygen. Determining the presence of the constituent in the fuel tank ullage based on the determined amount of absorption of the at least one wavelength can include determining the presence of oxygen based on the determined amount of absorption of the absorption wavelength of oxygen.

Determining the presence of the constituent in the fuel tank ullage based on the determined amount of absorption of the at least one wavelength can include determining an amount of the constituent present in the fuel tank ullage based on the determined amount of absorption of the at least one wavelength. Determining the operational status of the inert gas generating system can include determining the operational status corresponding to a failure mode of the inert gas generating system in response to determining that the amount of the constituent present in the fuel tank ullage deviates from one or more threshold acceptability criteria.

The one or more threshold acceptability criteria can include a threshold maximum limit corresponding to a maximum acceptable amount of the constituent. Determining that the amount of the constituent present in the fuel tank ullage deviates from the one or more threshold acceptability criteria can include determining that the amount of the constituent present in the fuel tank ullage exceeds the threshold maximum limit corresponding to the maximum acceptable amount of the constituent.

The one or more threshold acceptability criteria can include a threshold minimum limit corresponding to a minimum acceptable amount of the constituent. Determining that the amount of the constituent present in the fuel tank ullage deviates from the one or more threshold acceptability criteria can include determining that the amount of the constituent present in the fuel tank ullage is less than the threshold minimum limit corresponding to the minimum acceptable amount of the constituent.

A system can include a light source, at least one processor, and computer-readable memory. The light source can be located to transmit light through a fuel tank ullage. The computer-readable memory can be encoded with instructions that, when executed by the at least one processor, cause the system to: transmit the light from the light source through the fuel tank ullage; determine an amount of absorption of at least one wavelength of the transmitted light; and determine, based on the amount of absorption of the at least one wavelength of the transmitted light, a chemical composition of the fuel tank ullage.

The system of the preceding paragraph can optionally include, additionally and/or alternatively, any one or more of the following features, configurations, operations, and/or additional components:

The system can further include an image sensing device located to receive the transmitted light after the light is transmitted through the fuel tank ullage. The computer-readable memory can be further encoded with instructions that, when executed by the at least one processor, cause the system to determine the amount of absorption of the at least one wavelength of the transmitted light by at least causing the system to: measure an intensity of the at least one wavelength received at the image sensing device; measure an intensity of the at least one wavelength transmitted by the light source; and determine the amount of absorption of the at least one wavelength based on a change between the measured intensity of the at least one wavelength transmitted by the light source and the measured intensity of the at least one wavelength received at the image sensing device.

The image sensing device can be disposed at a location that is remote from the light source.

The image sensing device can be co-located with the light source to receive a reflection of the transmitted light after the transmitted light is reflected from a location that is a distance from the light source.

The computer-readable memory can be further encoded with instructions that, when executed by the at least one processor, cause the system to: determine the chemical composition of the fuel tank ullage by at least causing the system to determine presence of a constituent in the fuel tank ullage based on the determined amount of absorption of the at least one wavelength; and determine, based on the determined presence of the constituent in the fuel tank ullage, an operational status of an inert gas generating system configured to produce oxygen-depleted air for the fuel tank ullage.

The at least one wavelength of the transmitted light can include an absorption wavelength of oxygen. The computer-readable memory can be further encoded with instructions that, when executed by the at least one processor, cause the system to determine the presence of the constituent in the fuel tank ullage based on the determined amount of absorption of the at least one wavelength by at least causing the system to determine the presence of oxygen based on the determined amount of absorption of the absorption wavelength of oxygen.

The computer-readable memory can be further encoded with instructions that, when executed by the at least one processor, cause the system to: determine the presence of the constituent in the fuel tank ullage by at least causing the system to determine an amount of the constituent present in the fuel tank ullage based on the determined amount of absorption of the at least one wavelength; and determine the operational status of the inert gas generating system by at least causing the system to determine the operational status corresponding to a failure mode of the inert gas generating system in response to determining that the amount of the constituent present in the fuel tank ullage deviates from one or more threshold acceptability criteria.

The one or more threshold acceptability criteria can include a threshold maximum limit corresponding to a maximum acceptable amount of the constituent. The computer-readable memory can be further encoded with instructions that, when executed by the at least one processor, cause the system to determine that the amount of the constituent present in the fuel tank ullage deviates from the one or more threshold acceptability criteria by at least causing the system to determine that the amount of the constituent present in the fuel tank ullage exceeds the threshold maximum limit corresponding to the maximum acceptable amount of the constituent.

The one or more threshold acceptability criteria can include a threshold minimum limit corresponding to a minimum acceptable amount of the constituent. The computer-readable memory can be further encoded with instructions that, when executed by the at least one processor, cause the system to determine that the amount of the constituent present in the fuel tank ullage deviates from the one or more threshold acceptability criteria by at least causing the system to determine that the amount of the constituent present in the fuel tank ullage is less than the threshold minimum limit corresponding to the minimum acceptable amount of the constituent.

A device can include at least one processor and computer-readable memory. The computer-readable memory can be encoded with instructions that, when executed by the at least one processor, cause the device to: determine an amount of absorption of at least one wavelength of light transmitted from a light source through a fuel tank ullage; and determine, based on the amount of absorption of the at least one wavelength of the transmitted light, a chemical composition of the fuel tank ullage.

The device of the preceding paragraph can optionally include, additionally and/or alternatively, any one or more of the following features, configurations, operations, and/or additional components:

The computer-readable memory can be further encoded with instructions that, when executed by the at least one processor, cause the device to determine the amount of absorption of the at least one wavelength of the transmitted light by at least causing the device to determine the amount of absorption of the at least one wavelength of the transmitted light based on a change between a measured intensity of the at least one wavelength transmitted by the light source and a measured intensity of the at least one wavelength received at an image sensing device after the light is transmitted through a distance of the fuel tank ullage.

A method can include generating first image data representing a first field of view of an interior of a fuel tank using a first image capturing device disposed at an upper portion of the interior of the fuel tank, and generating second image data representing a second field of view of the interior of the fuel tank using a second image capturing device disposed at a lower portion of the interior of the fuel tank. The method can further include producing, by a processing device, a fuel measurement value representing an amount of fuel contained in the fuel tank based on the first image data and the second image data, and outputting, by the processing device, an indication of the fuel measurement value.

The method of the preceding paragraph can optionally include, additionally and/or alternatively, any one or more of the following features, configurations, operations, and/or additional components:

The first field of view of the interior of the fuel tank can include the lower portion of the interior of the fuel tank. The second field of view of the interior of the fuel tank can include the upper portion of the interior of the fuel tank.

Generating the first image data can include illuminating the first field of view using a light source disposed at the upper portion of the interior of the fuel tank.

Generating the first image data can include illuminating the first field of view using a light source disposed at the lower portion of the interior of the fuel tank.

Generating the second image data representing the second field of view including the upper portion of the interior of the fuel tank can include illuminating the second field of view using a light source disposed at the lower portion of the interior of the fuel tank.

Generating the second image data representing the second field of view including the upper portion of the interior of the fuel tank can include illuminating the second field of view using a light source disposed at the upper portion of the interior of the fuel tank.

Generating the first image data representing the first field of view including the lower portion of the interior of the fuel tank and generating the second image data representing the second field of view including the lower portion of the interior of the fuel tank can include generating the first image data and the second image data when an interface between fuel contained in the fuel tank and ullage of the fuel tank separates the first image capturing device and the second image capturing device.

Producing the fuel measurement value representing the amount of fuel contained in the fuel tank based on the first image data and the second image data can include identifying, based on the first image data and the second image data, a location of the interior of the fuel tank that intersects the interface between the fuel contained in the fuel tank and the ullage of the fuel tank.

Producing the fuel measurement value representing the amount of fuel contained in the fuel tank based on the first image data and the second image data further can include determining, based on a model of a shape of the fuel tank, a volume of fuel beneath the location of the interior of the fuel tank that intersects the interface between the fuel contained in the fuel tank and the ullage of the fuel tank.

A system can include a first image capturing device, a second image capturing device, at least one processor, and computer-readable memory. The first image capturing device can be disposed at an upper portion of an interior of a fuel tank. The second image capturing device can be disposed at a lower portion of the interior of the fuel tank. The computer-readable memory can be encoded with instructions that, when executed by the at least one processor, cause the system to: generate, using the first image capturing device, first image data representing a first field of view of the interior of a fuel tank; generate, using the second image capturing device, second image data representing a second field of view of the interior of the fuel tank; produce a fuel measurement value representing an amount of fuel contained in the fuel tank based on the first image data and the second image data; and output an indication of the fuel measurement value.

The system of the preceding paragraph can optionally include, additionally and/or alternatively, any one or more of the following features, configurations, operations, and/or additional components:

The first field of view of the interior of the fuel tank can include the lower portion of the interior of the fuel tank. The second field of view of the interior of the fuel tank can include the upper portion of the interior of the fuel tank.

The system can further include a light source disposed at the upper portion of the interior of the fuel tank. The computer-readable memory can be further encoded with instructions that, when executed by the at least one processor, cause the system to generate the first image data representing the first field of view including the lower portion of the interior of the fuel tank by at least causing the system to illuminate the first field of view using the light source disposed at the upper portion of the interior of the fuel tank.

The system can further include a light source disposed at the lower portion of the interior of the fuel tank. The computer-readable memory can be further encoded with instructions that, when executed by the at least one processor, cause the system to generate the first image data representing the first field of view including the lower portion of the interior of the fuel tank by at least causing the system to illuminate the first field of view using the light source disposed at the lower portion of the interior of the fuel tank.

The system can further include a light source disposed at the lower portion of the interior of the fuel tank. The computer-readable memory can be further encoded with instructions that, when executed by the at least one processor, cause the system to generate the second image data representing the second field of view including the upper portion of the interior of the fuel tank by at least causing the system to illuminate the second field of view using the light source disposed at the lower portion of the interior of the fuel tank.

The system can further include a light source disposed at the upper portion of the interior of the fuel tank. The computer-readable memory can be further encoded with instructions that, when executed by the at least one processor, cause the system to generate the second image data representing the second field of view including the upper portion of the interior of the fuel tank by at least causing the system to illuminate the second field of view using the light source disposed at the upper portion of the interior of the fuel tank.

The computer-readable memory can be further encoded with instructions that, when executed by the at least one processor, cause the system to generate the first image data representing the first field of view including the lower portion of the interior of the fuel tank and generate the second image data representing the second field of view including the lower portion of the interior of the fuel tank by at least causing the system to generate the first image data and the second image data when an interface between fuel contained in the fuel tank and ullage of the fuel tank separates the first image capturing device and the second image capturing device.

The computer-readable memory can be further encoded with instructions that, when executed by the at least one processor, cause the system to produce the fuel measurement value representing the amount of fuel contained in the fuel tank based on the first image data and the second image data by at least causing the system to identify, based on the first image data and the second image data, a location of the interior of the fuel tank corresponding to the interface between the fuel contained in the fuel tank and the ullage of the fuel tank.

The computer-readable memory can be further encoded with instructions that, when executed by the at least one processor, cause the system to produce the fuel measurement value representing the amount of fuel contained in the fuel tank based on the first image data and the second image data by at least causing the system to determine, based on a model of a shape of the fuel tank, a volume of fuel beneath the location of the interior of the fuel tank that corresponds to the interface between the fuel contained in the fuel tank and the ullage of the fuel tank.

A device can include at least one processor and computer-readable memory. The computer-readable memory can be encoded with instructions that, when executed by the at least one processor, cause the device to: produce a fuel measurement value representing an amount of fuel contained in a fuel tank based on first image data representing a first field of view of an interior of the fuel tank generated by a first image capturing device disposed at an upper portion of the interior of the fuel tank and second image data representing a second field of view of the interior of the fuel tank generated by a second image capturing device disposed at a lower portion of the interior of the fuel tank; and output an indication of the fuel measurement value.

The device of the preceding paragraph can optionally include, additionally and/or alternatively, any one or more of the following features, configurations, operations, and/or additional components:

The first field of view of the interior of the fuel tank can include the lower portion of the interior of the fuel tank. The second field of view of the interior of the fuel tank can include the upper portion of the interior of the fuel tank.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method comprising:
   emitting, from a light source, directional light through fuel contained in a fuel tank;
   determining a refraction angle of the directional light after the directional light passes through an interface with the fuel;
   determining, by a processing device, an index of refraction of the fuel based on the determined refraction angle; and
   determining, by the processing device, a density of the fuel based on the determined index of refraction of the fuel;
   wherein determining the refraction angle of the directional light comprises:
      identifying, using an image capturing device, a location of an interior of the fuel tank intersected by the directional light after the directional light passes through the interface with the fuel; and
      determining a distance between the location of the interior of the fuel tank intersected by the directional light and a location of the interior of the fuel tank corresponding to non-refraction of the directional light.

2. The method of claim 1, further comprising:
producing, by the processing device, a fuel measurement value representing an amount of fuel contained in the fuel tank based on the determined density of the fuel; and
outputting, by the processing device, an indication of the fuel measurement value.

3. The method of claim 2,
wherein producing the fuel measurement value representing the amount of fuel contained in the fuel tank based on the determined density of the fuel comprises determining a mass of the fuel contained in the fuel tank based on a determined volume of the fuel contained in the fuel tank and the determined density of the fuel.

4. The method of claim 1, further comprising:
measuring, using a thermal imaging device, a temperature of the fuel;
wherein determining the density of the fuel based on the determined index of refraction of the fuel comprises determining the density of the fuel based on the determined index of refraction of the fuel and the measured temperature of the fuel.

5. The method of claim 1,
wherein the interface with the fuel comprises an interface between the fuel and ullage gas of the fuel tank.

6. A system comprising:
a light source configured to emit directional light;
an image capturing device located to include a field of view of an interior of a fuel tank;
at least one processor; and
computer-readable memory encoded with instructions that, when executed by the at least one processor, cause the system to:
    emit the directional light from the light source through fuel contained in the fuel tank;
    determine a refraction angle of the directional light after the directional light passes through an interface with the fuel by at least causing the system to:
        generate image data of the interior of the fuel tank using the image capturing device;
        identify, using the image data, a location of the interior of the fuel tank intersected by the directional light after the directional light passes through the interface with the fuel; and
        determine, using the image data, a distance between the location of the interior of the fuel tank intersected by the directional light and a location of the interior of the fuel tank corresponding to non-refraction of the directional light;
    determine an index of refraction of the fuel based on the measured refraction angle; and
    determine a density of the fuel based on the determined index of refraction of the fuel.

7. The system of claim 6,
wherein the computer-readable memory is further encoded with instructions that, when executed by the at least one processor, cause the system to:
    produce a fuel measurement value representing an amount of fuel contained in the fuel tank based on the determined density of the fuel; and
    output an indication of the fuel measurement value.

8. The system of claim 7,
wherein the computer-readable memory is further encoded with instructions that, when executed by the at least one processor, cause the system to produce the fuel measurement value representing the amount of fuel contained in the fuel tank based on the determined density of the fuel by at least causing the system to determine a mass of the fuel contained in the fuel tank based on a determined volume of the fuel contained in the fuel tank and the determined density of the fuel.

9. The system of claim 6, further comprising:
a thermal imaging device located to include a field of view of an interior of the fuel tank;
wherein the computer-readable memory is further encoded with instructions that, when executed by the at least one processor, cause the system to determine the density of the fuel based on the determined index of refraction of the fuel by at least causing the system to determine the density of the fuel based on the determined index of refraction of the fuel and a temperature of the fuel measured using the thermal imaging device.

10. The system of claim 6,
wherein the interface with the fuel comprises an interface between the fuel and ullage gas of the fuel tank.

11. A device comprising:
at least one processor; and
computer-readable memory encoded with instructions that, when executed by the at least one processor, cause the device to:
    determine a refraction angle of directional light emitted from a light source through fuel contained in a fuel tank after the directional light passes through an interface with the fuel;
    determine an index of refraction of the fuel based on the measured refraction angle by at least causing the device to:
        identify, using the image data generated by an image capturing device located to include a field of view of the interior of the fuel tank, a location of the interior of the fuel tank intersected by the directional light after the directional light passes through the interface with the fuel; and
        determine, using the image data, a distance between the location of the interior of the fuel tank intersected by the directional light and a location of the interior of the fuel tank corresponding to non-refraction of the directional light; and
    determine a density of the fuel based on the determined index of refraction of the fuel.

12. The device of claim 11,
wherein the computer-readable memory is further encoded with instructions that, when executed by the at least one processor, cause the device to:
    produce a fuel measurement value representing an amount of fuel contained in the fuel tank based on the determined density of the fuel; and
    output an indication of the fuel measurement value.

13. The device of claim 12,
wherein the computer-readable memory is further encoded with instructions that, when executed by the at least one processor, cause the device to produce the fuel measurement value representing the amount of fuel contained in the fuel tank based on the determined density of the fuel by at least causing the system to determine a mass of the fuel contained in the fuel tank based on a determined volume of the fuel contained in the fuel tank and the determined density of the fuel.

14. The device of claim 11,
wherein the computer-readable memory is further encoded with instructions that, when executed by the at least one processor, cause the device to determine the density of the fuel based on the determined index of refraction of the fuel by at least causing the device to determine the density of the fuel based on the determined index of refraction of the fuel and a temperature of the fuel measured using a thermal imaging device.

\* \* \* \* \*